US012697022B2

(12) United States Patent
Al-Aswad et al.

(10) Patent No.: US 12,697,022 B2
(45) Date of Patent: Aug. 4, 2026

(54) VISUAL FIELD SYSTEMS AND METHODS FOR GLAUCOMA DIAGNOSIS AND MONITORING BY IMPLEMENTING ADAPTIVE MAP PERIMETRY VIA HEAD-MOUNTED DISPLAYS

(71) Applicant: ENVISION HEALTH TECHNOLOGIES INC., Brooklyn, NY (US)

(72) Inventors: Lama Al-Aswad, Philadelphia, PA (US); Iván Marín-Franch, Atarfe (ES)

(73) Assignee: ENVISION HEALTH TECHNOLOGIES INC., Brooklyn, NY (US)

( * ) Notice: Subject to any disclaimer, the term of this patent is extended or adjusted under 35 U.S.C. 154(b) by 0 days.

(21) Appl. No.: 19/410,291

(22) Filed: Dec. 5, 2025

(65) Prior Publication Data

US 2026/0083317 A1    Mar. 26, 2026

Related U.S. Application Data

(63) Continuation of application No. PCT/US2024/062113, filed on Dec. 27, 2024.

(Continued)

(51) Int. Cl.
*A61B 3/00*        (2006.01)
*A61B 3/024*       (2006.01)
*A61B 3/113*       (2006.01)

(52) U.S. Cl.
CPC ............ *A61B 3/0025* (2013.01); *A61B 3/005* (2013.01); *A61B 3/024* (2013.01); *A61B 3/113* (2013.01)

(58) Field of Classification Search
CPC ........ A61B 3/0025; A61B 3/005; A61B 3/024
See application file for complete search history.

(56) References Cited

U.S. PATENT DOCUMENTS 6,494,578 B1    12/2002  Plummer et al.
11,311,188 B2   4/2022   Hooriani et al.
                 (Continued)

FOREIGN PATENT DOCUMENTS

WO      WO-90/01290 A1      2/1990
WO      WO-2018/107108 A1   6/2018

OTHER PUBLICATIONS

Asman et al., Spatial analyses of glaucomatous visual fields; a comparison with traditional visual field indices, Acta Ophthalmol (Copenh)., 70(5):679-86 (Oct. 1992).

(Continued)

*Primary Examiner* — Jack Dinh
(74) *Attorney, Agent, or Firm* — MARSHALL, GERSTEIN & BORUN LLP

(57)        ABSTRACT

A system may include a headset device and an average hill of vision model (HoV) and may generate an eye difference estimate relative to reference data for an average healthy eye obtained from a normative dataset. The eye difference estimate indicates a difference in overall sensitivity or general height and the rate of sensitivity decay with eccentricity relative to the reference data. The system may generate an individualized HoV model based on the eye difference estimate and the average HoV model, display, on the headset device, a respective stimulus at a plurality of test locations, store responses to the stimulus, and analyze the responses to determine a respective sensitivity value at each of the plurality of test locations. The system may determine total-deviation values by subtracting the respective sensitivity value from a corresponding value of the individualized HoV model, analyze the total-deviation values, and provide feedback based on the analysis.

20 Claims, 18 Drawing Sheets

Related U.S. Application Data

(60) Provisional application No. 63/673,383, filed on Jul. 19, 2024, provisional application No. 63/615,945, filed on Dec. 29, 2023.

(56) References Cited

U.S. PATENT DOCUMENTS

| | | |
|---|---|---|
| 2011/0194075 A1 | 8/2011 | Weleber et al. |
| 2019/0150727 A1 | 5/2019 | Blaha et al. |
| 2019/0231184 A1 | 8/2019 | Alawa |
| 2019/0298166 A1 | 10/2019 | Smith et al. |
| 2023/0284899 A1 | 9/2023 | Warburton et al. |
| 2023/0404385 A1 | 12/2023 | Kurz |

OTHER PUBLICATIONS

Blumenthal et al., Misleading statistical calculations in far-advanced glaucomatous visual field loss, Ophthalmology, 110(1):196-200 (Jan. 2003).

Bryan et al., Robust and censored modeling and prediction of progression in glaucomatous visual fields, Invest Ophthalmol Vis Sci., 54(10):6694-700 (Oct. 2013).

Drance et al., [Early defects in the visual field in glaucoma (author's transl)], Klin Monbl Augenheilkd., 173(4):519-23. Fruhe Gesichtsfeldausfalle bei Glaukomerkrankung (Oct. 1978).

Erler et al., Optimizing structure-function relationship by maximizing correspondence between glaucomatous visual fields and mathematical retinal nerve fiber models, Invest Ophthalmol Vis Sci., 55(4):2350-7 (Apr. 2014).

Gardiner et al., The Effect of Limiting the Range of Perimetric Sensitivities on Pointwise Assessment of Visual Field Progression in Glaucoma, Investigative Ophthalmology and Visual Science, 57(1): 288-294 (2016).

Held, Chapter 5 Computing Voronoi diagrams. In: Held M, ed. On the Computational Geometry of Pocket Machining. Springer Berlin Heidelberg; 1991:63-88.

Hermann et al., Age-dependent normative values for differential luminance sensitivity in automated static perimetry using the Octopus 101, Acta Ophthalmol., 86(4):446-55 (Jun. 2008).

International Patent Application No. PCT/US2024/062108, International Search Report and Written Opinion, date of mailing Mar. 5, 2025.

International Patent Application No. PCT/US2024/062110, International Search Report and Written Opinion, date of mailing Mar. 5, 2025.

International Patent Application No. PCT/US2024/062113, International Search Report and Written Opinion, date of mailing Mar. 6, 2025.

Jansonius et al., A mathematical description of nerve fiber bundle trajectories and their variability in the human retina, Vision Research, 49(17): 2157-2163 (2009).

Jansonius et al., A mathematical model for describing the retinal nerve fiber bundle trajectories in the human eye: Average course, variability, and influence of refraction, optic disc size and optic disc position, Experimental Eye Research, 105: 70-78 (2012).

Jansonius et al., Erratum to "A mathematical description of nerve fiber bundle trajectories and their variability in the human retina" [Vision Research 49(17) (2009) 2157--2163], Vision Research, 50: 1501 (2010).

King et al., An approach towards automated custom static perimetry, Investigative Ophthalmology & Visual Science, 64(8):5111 (2023).

King-Smith et al., Efficient and unbiased modifications of the Quest threshold method: theory, simulations, experimental evaluation and practical implementation, Vision Res., 34(7):885-912 (Apr. 1994).

Kucur et al., A deep learning approach to automatic detection of early glaucoma from visual fields, PLoS One, 13(11):e0206081 (2018).

Marin-Franch et al., A novel strategy for the estimation of the general height of the visual field in patients with glaucoma, Graefes Arch Clin Exp Ophthalmol., 252(5):801-9 (May 2014).

Marin-Franch et al., Analysis of global and focal loss in glaucoma progression, Rome, Italy: World Glaucoma Congress, 681-682 (2023).

Marin-Franch et al., The Open Perimetry Initiative: A framework for cross-platform development for the new generation of portable perimeters, J Vis., 22(5):1 (Apr. 2022).

Marin-Franch et al., The visualFields package: a tool for analysis and visualization of visual fields, J Vis., 13(4): 10 (Mar. 2013).

Marin-Franch et al., Using high-density perimetry to explore new approaches for characterizing visual field defects, Vision Res., 210:108259 (Sep. 2023).

Marin-Franch et al., Visual field progression in glaucoma: Comparison between PoPLR and Answers, Translational Vision Science and Technology, 10(14):13:1-7 (2021).

Montesano et al., A Comparison between the Compass Fundus Perimeter and the Humphrey Field Analyzer, Ophthalmology, 126(2):242-251 (Feb. 2019).

O'Leary et al., Visual field progression in glaucoma: estimating the overall significance of deterioration with permutation analyses of pointwise linear regression (PoPLR), Investigative Ophthalmology and Visual Science, 53(11):6776-84 (2012).

Peracha et al., Assessing the Reliability of Humphrey Visual Field Testing in an Urban Population, Investigative Ophthalmology & Visual Science, 54(15):3920-3920 (2013).

Rao et al., Role of visual field reliability indices in ruling out glaucoma, JAMA Ophthalmol., 133(1):40-4 (Jan. 2015).

Sloan, Area and luminance of test object as variables in examination of the visual field by projection perimetry, Vision Research, 1(1):121-IN2 (1961).

Turpin et al., Improving Personalized Structure to Function Mapping From Optic Nerve Head to Visual Field, Translational Vision Science and Technology, 10(1): 19 (2021).

Turpin et al., The Open Perimetry Interface: An enabling tool for clinical visual psychophysics, Journal of Vision, 12(11):22 (2012).

Wall et al., The Effective Dynamic Ranges for Glaucomatous Visual Field Progression With Standard Automated Perimetry and Stimulus Sizes {III} and {V}, Investigative Ophthalmology and Visual Science, 59(1): 439-445 (2018).

Watson et al., Quest: A Bayesian adaptive psychometric method, Perception & Psychophysics, 33(2):113-120 (1983).

Wu et al., Frequency of Testing to Detect Visual Field Progression Derived Using a Longitudinal Cohort of Glaucoma Patients, Ophthalmology, 124(6):786-792 (Jun. 2017).

Zemborain et al., Test of a Retinal Nerve Fiber Bundle Trajectory Model Using EyesWith Glaucomatous Optic Neuropathy, Translational Vision Science and Technology, 11(7): 7 (2022).

*300*

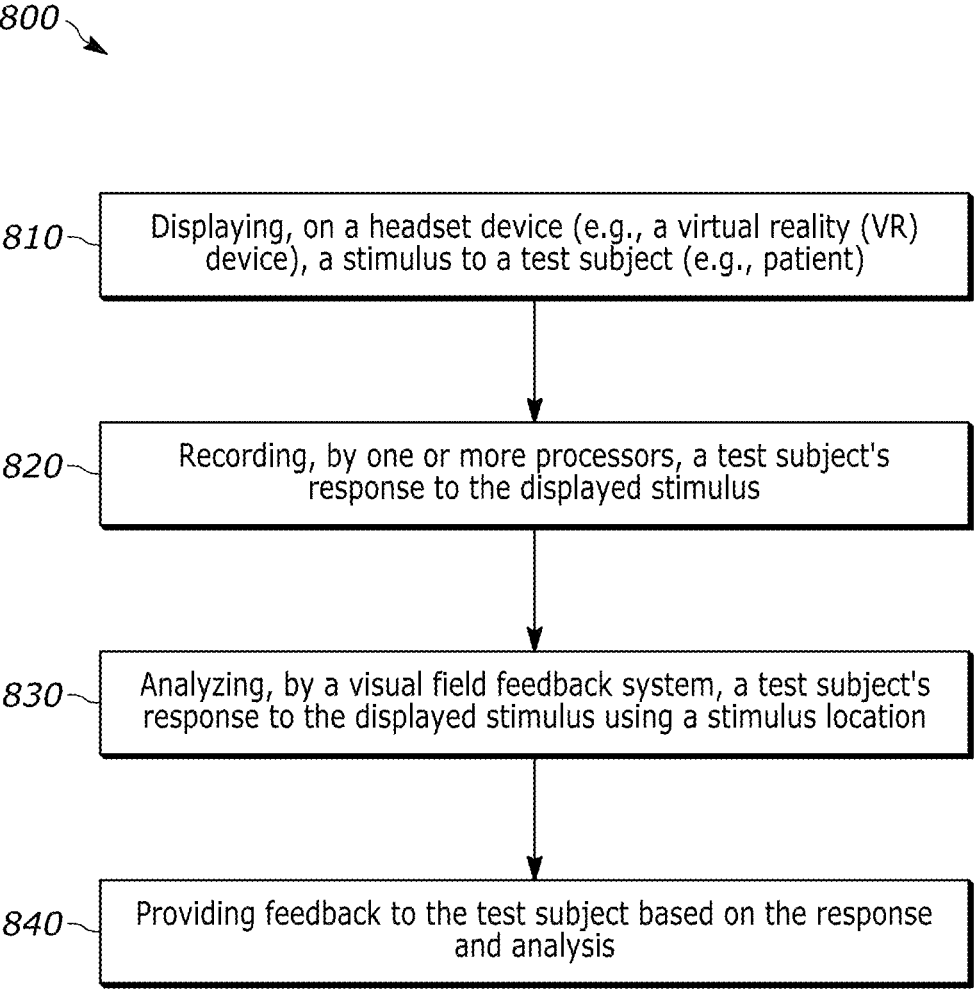

800

810 — Displaying, on a headset device (e.g., a virtual reality (VR) device), a stimulus to a test subject (e.g., patient)

820 — Recording, by one or more processors, a test subject's response to the displayed stimulus 830 — Analyzing, by a visual field feedback system, a test subject's response to the displayed stimulus using a stimulus location 840 — Providing feedback to the test subject based on the response and analysis

FIG. 8

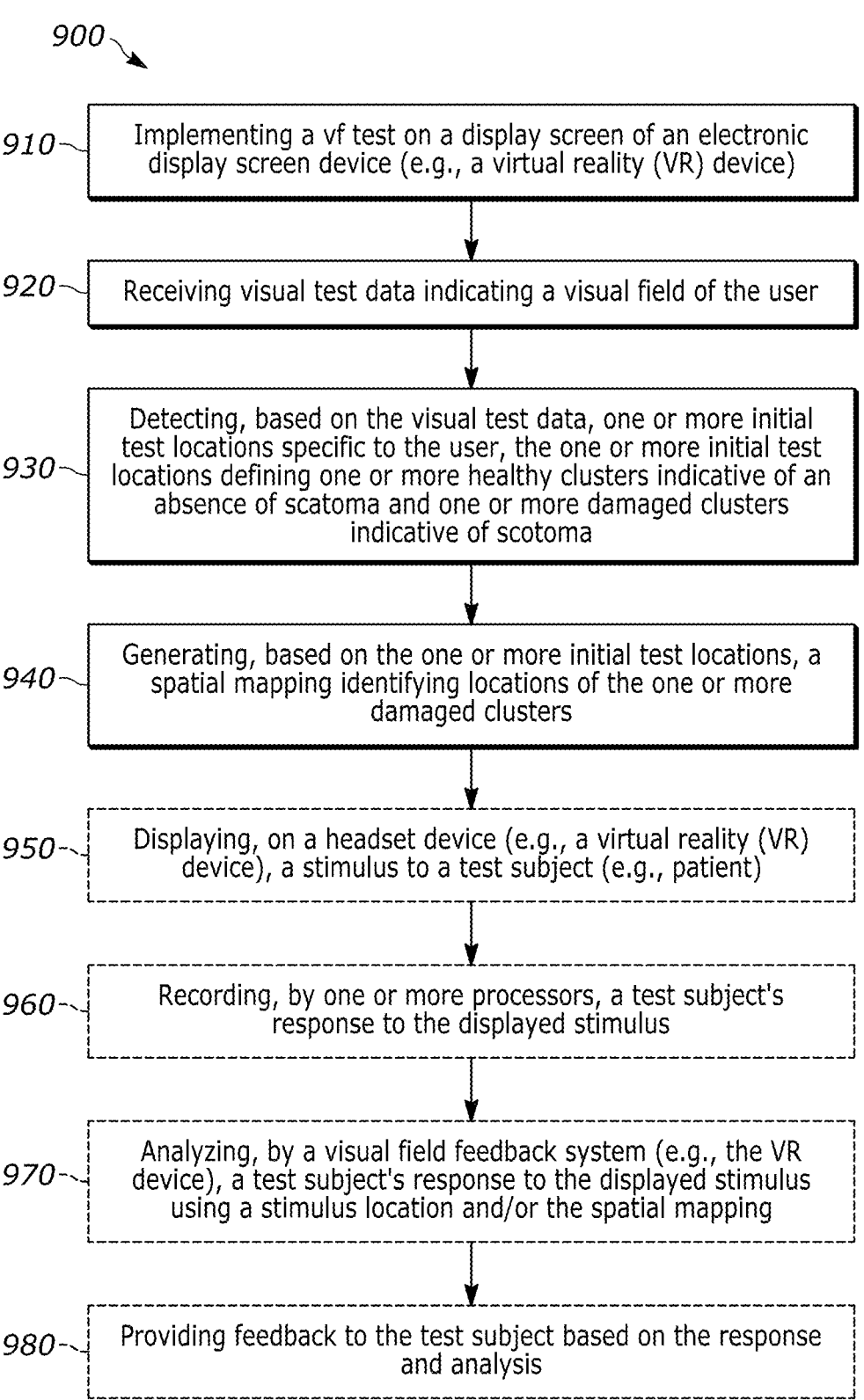

*900*

910 — Implementing a vf test on a display screen of an electronic display screen device (e.g., a virtual reality (VR) device)

920 — Receiving visual test data indicating a visual field of the user

930 — Detecting, based on the visual test data, one or more initial test locations specific to the user, the one or more initial test locations defining one or more healthy clusters indicative of an absence of scatoma and one or more damaged clusters indicative of scotoma 940 — Generating, based on the one or more initial test locations, a spatial mapping identifying locations of the one or more damaged clusters 950 — Displaying, on a headset device (e.g., a virtual reality (VR) device), a stimulus to a test subject (e.g., patient)

960 — Recording, by one or more processors, a test subject's response to the displayed stimulus 970 — Analyzing, by a visual field feedback system (e.g., the VR device), a test subject's response to the displayed stimulus using a stimulus location and/or the spatial mapping 980 — Providing feedback to the test subject based on the response and analysis

FIG. 9

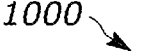
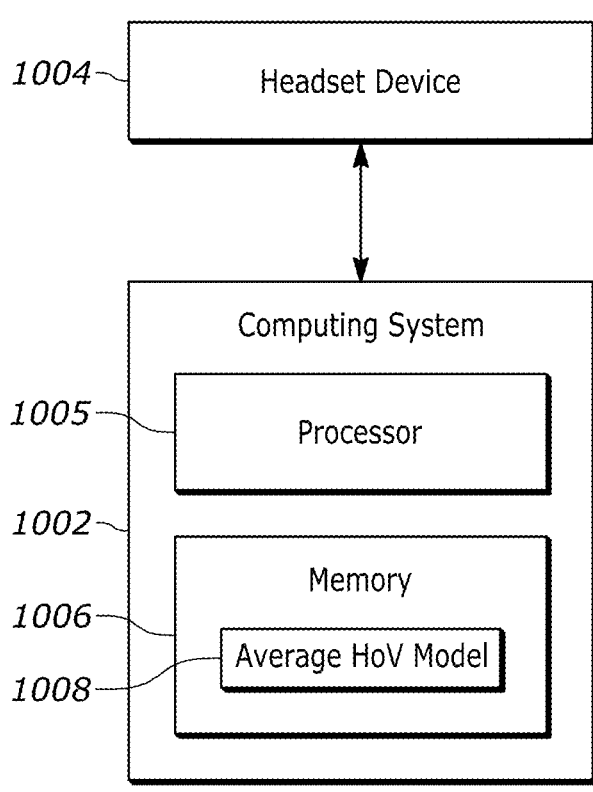
FIG. 10A

VISUAL FIELD SYSTEMS AND METHODS FOR GLAUCOMA DIAGNOSIS AND MONITORING BY IMPLEMENTING ADAPTIVE MAP PERIMETRY VIA HEAD-MOUNTED DISPLAYS

RELATED APPLICATIONS

This application claims the benefit of U.S. Provisional Application No. 63/615,945 (filed on Dec. 29, 2023), which is incorporated in its entirety by reference herein. This application also claims the benefit of U.S. Provisional Application No. 63/673,383 (filed on Jul. 19, 2024), which is incorporated in its entirety by reference herein. This application also claims the benefit of PCT Application No. PCT/US2024/062113 (filed on Dec. 27, 2024), which is incorporated in its entirety by reference herein.

FIELD OF THE DISCLOSURE

The present disclosure generally relates to systems and methods for glaucoma diagnosis and monitoring and relates, in particular, to virtual reality (VR) systems and methods for glaucoma diagnosis and monitoring by adaptive visual field (VF) analysis on head-mounted displays such as VR headsets or otherwise VR devices.

BACKGROUND

Glaucoma is a chronic, progressive eye disease caused by damage to the optic nerve, which can lead to VF loss. One of the major risk factors is eye pressure. An abnormality in the eye's drainage system can cause fluid to build up, leading to excessive pressure that causes damage to the optic nerve. Glaucoma is a leading cause of irreversible blindness and is challenging to diagnose, often resulting in late detection and irreversible vision loss. For example, 3 million Americans have glaucoma. This prevalence is expected to increase to 6.3 million individuals within the next 30 years with the aging population. As a disease that is asymptomatic in its early-moderate stages, glaucoma is challenging to diagnose. Early detection of visual changes is crucial to prevent vision loss; however, diagnosis and disease monitoring are complicated by the subjectivity of functional testing and limitations of current diagnostic methodology.

The primary goal of perimetry is to measure functional performance across the VF. Before the introduction of computers that allowed automated presentation of visual stimuli, this goal was achieved by manually moving small stimuli and finding the locations of transitions, called isopters, between the regions where a given stimulus was seen or not seen. These isopters produced a topographic map of the patient's hill of vision. A qualified clinician was required to perform the test. Visual inspection led to the identifications of anomalies of the topographic map caused by tumors pressing on the optic pathway, vascular damage in the central nervous system, and glaucoma, among others. Manual perimetry has several limitations. It requires a highly trained tester to administer the test accurately which both is costly and limits scalability. The test is also time consuming, for both the tester and patients and there is often a high level of variability between different testers, reducing the reliability and consistency of data, especially over time.

Such drawbacks led to the replacement, in glaucoma, of manual kinetic perimetry in favor of static automated perimetry (SAP), a test that was originally intended to complement kinetic perimetry. SAP offered a more uniform approach and removed reliance on a perimetrist. Testing uniformity allowed for a standardization in data analysis and interpretation, which became crucial in the success of the adoption of SAP over kinetic perimetry. SAP is, however, less reliant than kinetic perimetry in identifying spatial patterns of damage and in drawing comparisons with retinal examinations because of spatial under-sampling and high test-retest variability of contrast sensitivity thresholds in damaged regions estimated from a small number of stimulus presentations. The transition to SAP was only possible because of advances in hardware and software in the 70s and 80s permitted the development of algorithms and computationally intensive analytical tools, its limitations are a product of its time. Perimetry methods have not changed much since the 1980s, even though understanding of the structural and anatomical changes that occur in glaucoma has progressed greatly. The use, for instance, of regular grids of test locations that are so far apart from each other and out of sync with results from structural testing and other imaging methods, reduces our confidence in the clinical assessment in both detection of damage and progression. For patients, this delay translates to irreversible vision loss. Beyond this, providers struggle with the lack of reliability of results, often repeating VF testing at subsequent visits, to make treatment decisions. A reported 17% to 48% of VF tests results are unreliable due to high fixation losses, false positive, and false negative rates.

As a result, several problems or otherwise pain points emerge from the limitations of current diagnostic methodology. The current, most common VF testing paradigm, SAP, misses early disease and early changes in disease progression, leading to delayed intervention and progressive vision loss. In addition, at early stages, conventional SAP testing is prone to higher false positive rates, which means manifest field loss may be missed.

Still further, additional problems exist because providers must rely on diagnostic and monitoring tests that are sub-optimal/unreliable and imprecise, limiting ability to accurately determine progression. Functional defects are not characterized with consistency and do not often agree with anatomical changes, adding uncertainty to the diagnosis and management of glaucoma.

Still further, given the subjective nature of VF and/or functional testing for glaucoma, factors impacting the patient's experience can have a direct impact on a provider's ability to monitor the disease. Patients have difficulty completing conventional SAP testing for a variety of reasons including a lack of engagement. For example, a conventional test is tedious and requires close concentration and strict fixation on a central target, and can also require uncomfortable positioning, as patients must lean forward in a kyphotic position and remain there for the duration of testing, which negatively impact the reliability and repeatability of test results.

Accordingly, to address these problems, there is a need for systems and methods for glaucoma diagnosis and monitoring by adaptive VF analysis on head-mounted displays such as VR headsets.

BRIEF SUMMARY

The inventive disclosure herein provides revolutionary glaucoma diagnosis and monitoring systems and methods that implement a groundbreaking adaptive VF methods and analytical tools through head-mounted displays such as VR headsets. The innovations as described herein allow for improved testing that can capture functional changes alongside structural changes of a patient's eyes, and thus can be used in the field of eye care, health, and monitoring at a user-specific level of fidelity.

The headset-based systems, methods, and analytical tools of the present disclosure provide a groundbreaking shift in glaucoma diagnostics by providing perimetry for glaucoma diagnosis and monitoring. The headset-based systems and methods comprise autonomous systems and methods that can detect regions of interest (e.g., areas of the retina known or suspected to be damaged) and implement spatial analysis to iteratively select new locations for testing. Such spatial analysis can generate data for spatial mapping of defect scotomata. Such spatial mapping provides high fidelity analysis and output comprising a much greater resolution than a conventional 24-2 pattern of test locations for a user's eyes. The spatial mapping of scotomata is implemented as adaptive and unique for each user (i.e., user-specific) and the results can detect or identify structural defects.

One key feature of implementation of the headset-based systems and methods, as described herein, is that, unlike conventional SAP, where locations are separated by 6° of visual angle vertically and horizontally and 8.5° diagonally, the headset-based systems and methods operating on VR headsets that implement an adaptive map perimetry algorithm can test locations separated by as little as 0.5°; a resolution that is 12 to 17 times greater than SAP for the typical Goldmann size III stimulus, with a radius of 0.43°. Resolution can be as small as 0.1° for smaller stimuli (e.g., Goldmann size I with a radius of ~0.1°), depending on the limitations of the headset's display. Such high-fidelity implementation yields an improved sensitivity for detecting spatial progression in scotomata. In addition, the headset-based systems and methods of the present disclosure provides one or more improvements compared to conventional SAP, where conventional SAP disadvantageously presents stimuli in fixed locations regardless of retinal structure. By contrast, headset-based systems and methods solution introduces a novel, user-specific approach that can adapt in real-time as the patient undergoes testing. The headset-based systems and methods are differentiated from conventional methodologies by implementing adaptive map perimetry in a technical manner that makes such testing practical and accessible, and that significantly enhances the granularity and accuracy of glaucoma progression monitoring.

In accordance with the above, and with the disclosure herein, the present disclosure includes improvements in computer functionality or in improvements to other technologies at least because the disclosure recites that, e.g., the field of glaucoma diagnosis and monitoring is improved through implementation of an adaptive map perimetry algorithm implemented for execution on a headset device, which enhances image granularity and accuracy of glaucoma progression monitoring. Still further, the headset itself is improved by installing or implementing a normative database and/or model configured to adapt the headset to implement the adaptive map perimetry algorithm device-agnostic with respect to other, differently configured headset, each of which may have different hardware configurations and subsequently limitations. That is, the normative model, and/or its related normative database, allows for the adaptive map perimetry algorithm to be implemented on a variety of headsets despite their differences in hardware and limitations, including display screen, field of view, processors, or the like. This improves over the prior art at least because conventional methods for glaucoma monitoring lack the adaptivity and precision provided by the adaptive map perimetry algorithm as implemented on a headset.

Still further, the present disclosure includes applying the certain of the elements with, or by use of, a particular machine, e.g., a VR headset or device or other head-mounted display.

The present disclosure includes specific features other than what is well-understood, routine, conventional activity in the field, and/or otherwise adds unconventional steps that confine the disclosure to a particular useful application, e.g., systems and methods for glaucoma diagnosis and monitoring by adaptive VF analysis on head-mounted displays such as VR headsets.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein:

FIG. 8 illustrates an example visual field feedback (VFF) method for automatically assessing visual field testing in accordance with various embodiments herein.

FIG. 9 illustrates a further example VF analysis method for glaucoma diagnosis and monitoring by implementing adaptive map perimetry and, optionally performing visual field testing in in accordance with various embodiments herein.

FIG. 10A illustrates a diagram of a visual field analysis (VFA) system in accordance with various embodiments herein.

Figure 1:
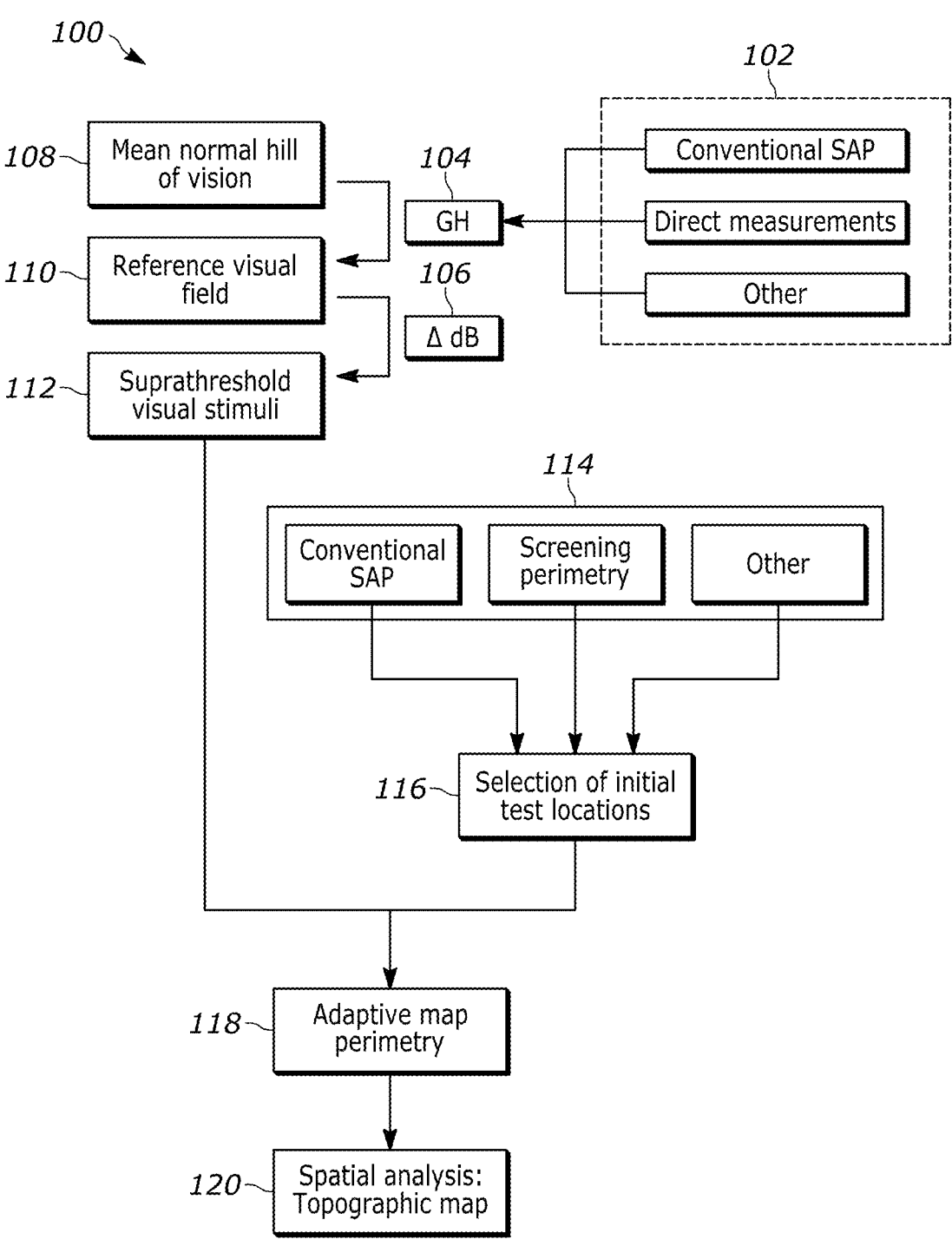
FIG. 1 illustrates an example method for glaucoma diagnosis and monitoring by adaptive VF analysis on head-mounted displays such as VR headsets, in accordance with various embodiments of the present disclosure.

The Figures depict preferred embodiments for purposes of illustration only. Alternative embodiments of the systems and methods illustrated herein may be employed without departing from the principles of the invention described herein.

DETAILED DESCRIPTION

The VR systems and methods described herein implement an innovative and automated adaptive VF test, to enable earlier disease detection and identification of glaucomatous disease progression. The adaptive strategy described herein provides high fidelity image data insights into VF defects allowing for a level of optimization of patient care that is currently unavailable, through the personalization of treatment and monitoring. The VR systems and methods use VR technology to create a patient-centric solution that overcome problems inherent in conventional technologies in the field of glaucoma.

The VR systems and methods described herein implement adaptive map perimetry that provides an advancement in glaucoma testing. The VR systems and methods implement an automated adaptive VF test for diagnosing, and testing in real-time, glaucoma. Such VR systems and methods can use or can input user-specific data rather than conventional reference data, the latter of which can be susceptible to a greater amount of false positives.

Glaucoma is not uniform in how it behaves from one patient to the next. Accordingly, the VR systems and methods implement a VF test that is specific to a given user or patient. The VR systems and methods described herein implement a headset-based VF test with using an adaptive perimetric algorithm that is adaptive and user-specific (e.g., patient centric). The adaptive map perimetry algorithm provides automation and uniformity through data analysis as well as individualization and an enhanced ability to map spatial patterns (e.g., create or otherwise determine a spatial mapping) of damage of a user's eyes, without the need for a highly trained clinician. The adaptive map perimetry algorithm uses anatomical models of retinal nerve trajectories (e.g., a Jansonius map) and glaucoma pathophysiology to adapt itself depending on the patient's responses during runtime. This diverges greatly from the conventional VF testing methods, which do not adapt to the patient's stage or specific patterns of damage of the eyes. In this way, the VR systems and methods implement a patient-centric approach to disease characterization.

In addition to this implementation, the VR systems and methods described herein provide active fixation correction with eye tracking and a gaming interface for testing and improving reliability. For example, implementation of gamification in a VR setting makes testing easier and more enjoyable for the patient, which, importantly improves engagement and concentration and, therefore, data fidelity, which can eliminate false positive and/or false negative responses or other errors. By contrast, one of the most significant issues with conventional SAP is the reliability of test results. For example, a retrospective study among patients with glaucoma found roughly 48% of Humphrey Field Analyzer (HFA) based tests to be unreliable. This is attributed commonly to fixation losses, which are complicated by factors such as fatigue and boredom, and which directly affect results. With more reliable VF results as provided by the VR systems and methods described herein, test-retest variability may be improved, in addition to the specificity of the VF test. The VR systems and methods of the present disclosure also address issues related to poor engagement, where several elements of gamification can be applied including feedback mechanisms, immersive environments, progression trackers/reflectors, point scoring systems, and stylized interfaces. These elements improve user engagement and concentration, and therefore output of the device.

The VR systems and methods described herein are configured to be device-agnostic, e.g., configured to be executed on headsets or otherwise VR devices with different characteristics, hardware, and/or limitations. This is accomplished through implementation of the adaptive map perimetry algorithm executed by one or more processors communicatively coupled to a head-mounted device (including VR headsets). The head-mounted device (including VR headsets) can be one of many head-mounted devices, each having different configurations, such as different hardware (e.g., displays, cameras, sensors, mounting hardware, and/or variations thereof). The adaptive map perimetry algorithm adapts to the specific configuration and limitation of the headset to operate uniformity regardless of hardware and/or limitations, in such a way that the VR systems and methods are adaptive, across various devices. In this way, with minimal effort, the adaptive map perimetry algorithm can be procedurally optimized accounting for, adapted to, or otherwise based on the limitations of each individual device. In various implementations, the adaptive map perimetry algorithm is configured to identify scotomata of various types, including by way of non-limiting example, paracentral, arcuate, nasal, altitudinal, and other types of scotomata despite hardware differences of one or more VR devices. Additionally, or alternatively, in some implementations, the adaptive map perimetry algorithm may also be configured or programmed to be executed on other electronic device, which may include by way of non-limiting example, tablet devices, computer screens, or other electronic devices having screens for display or rendering of graphical images or content (e.g., VR content) as described herein.

The VR systems and methods can also provide adaptability, across different headset and/or VR devices, through implementation and use of a normative database and/or proprietary normative reference model, for example, as described herein. For example, an observational study was conducted on eyes of subjects that utilizes the adaptive map perimetry algorithm. In various aspects, the adaptive map perimetry algorithm comprises a suprathreshold algorithm that uses normative data obtained from or otherwise output by a ZEST algorithm. That is, in various aspects, the adaptive map perimetry algorithm can use normative data, e.g., of a normative database and/or normative model (as provided as output from a ZEST algorithm), to identify healthy regions of the retina in previous visual field tests for the estimation of the patient's general height (GH) of. For a more optimal use, the adaptive algorithm includes estimating GH from fast direct measurements of the eyes. Uniform analytical mappings, tools, and visual aids may be used for display or otherwise interpretation of VF results based on output of the adaptive.

Example Adaptive Map Perimetry Algorithm

This section describes an example adaptive map perimetry algorithm. It should be noted that the example herein describes one implementation of the adaptive map perimetry algorithm, and that other, different implementations may also be used. In the present example, the adaptive map perimetry algorithm comprises a suprathreshold test that requires VF locations that are at least suspected of having functional damage as a seed, e.g., an estimation of the GH to get a reference VF from which to derive the location-dependent suprathreshold levels.

In some implementations, the adaptive map perimetry algorithm implements a model of glaucoma pathophysiology. The adaptive map perimetry algorithm may also integrate active eye corrections and use a normative model and/or normative database for the selection of suprathreshold visual stimuli. The adaptive map perimetry algorithm may further automate methods for the selection of initial VF locations. The initial VF locations, the suprathreshold visual stimuli, and/or other parameters may be used, as input, by the adaptive map perimetry algorithm to identify iteratively the locations that are damaged by presenting or displaying (e.g., via a display of the VR device) visual stimuli once or twice and recording whether the patient responded to the first trial (in which case the algorithm stops for this location), or missed one or both of the visual stimuli.

Spatial analyses on clusters of damaged locations from previous VF SAP tests (e.g., 24-2, 30-2, 10-2, adaptive perimetry) can be used to determine the set of initial test locations for the adaptive map perimetry algorithm. The spatial analysis may be used to obtain clusters of damaged locations and identifying the upper and lower delimiting locations (e.g., cluster edges), for example, as shown and described for FIG. 2A. The adaptive map perimetry algorithm may further be confirmed to, for each cluster, estimate the shape and size of the scotoma by fitting the retinal nerve fiber bundle trajectories to the cluster edges (FIG. 2A) thus individualizing the Jansonius structure-function map (FIG. 3A) to the patient's anatomy and specific defective regions. A preliminary set of possible test locations may be determined for use by the adaptive algorithm depending on a given vertical and horizontal resolution, e.g., 2° as in FIG. 2 B. The adaptive map perimetry algorithm may select all or some of these locations as initial pool of test locations. The adaptive map perimetry algorithm may update iteratively the estimated scotomata depending on user's responses and new untested locations may be included or dropped from the initial pool. The resolution between locations may be varied between 0.1° (about the size of Goldmann Size I) and 6° (e.g., the separation in the 24-2 and 30-2 regular grids).

In should be noted that additional and/or different suprathreshold values and/or strategies may be used. Still further, in some implementations, spatial analysis of clusters of damaged locations can be implemented based on Voronoi tessellation. In addition, in some implementations, instead of using the Jansonius map, which can provide average bundle paths to an otherwise variable population, the Jansonius map or otherwise values can be used to obtain individualized fits. In some implementations, selection of new test locations can go beyond the upper and lower bundle to ensure that the patient can see visual stimuli there, e.g., thereby confirming the scotoma edge). The adaptive map perimetry algorithm can stop when either all tested locations surrounding a scotoma are deemed not damaged or it reaches the limits of the test region as determined by an operator.

FIG. 1 illustrates an example workflow an example implementation of an adaptive map perimetry algorithm. At block 102, parameters or values comprising conventional SAP values, direct measurements of the eyes, or other values are captured with respect to measuring glaucoma. Such parameters or values are provided as input for the adaptive map perimetry algorithm to produce an estimated GH value 104. A mean normal hill of vision value 108 is analyzed with a reference VF value 110 to generate a AdB value 106, which is the decrement in attenuation (in dB) for generating a suprathreshold visual stimuli value 112. The suprathreshold visual stimuli value 112 can used at each location of the VF. At block 114, various techniques 114 (e.g., including conventional SAP, screening perimetry, and other such techniques) can be used to select (block 116) initial test locations. At block 118, the initial test locations, in addition to the visual stimuli value 112, are provided as input to an adaptive map perimetry algorithm, which can be implemented for any type of spatial glaucomatous damage and use available patient's results who have previously undergone the conventional (24-2, 10-2, 30-2) perimetry or (suprathreshold) screening test. The adaptive map perimetry algorithm can use the initial test locations to perform adaptive map perimetry. The output of the adaptive map perimetry can then be analyzed to perform spatial analysis for generating a topographic map 120 with summary statistics of glaucomatous damage of the user's eye.

Example Determination of Parameters for the Adaptive Map Perimetry Algorithm The adaptive map perimetry algorithm can be configured to input various parameters or values to adapt the algorithm for specific device(s) and/or users. In this way, the adaptive map perimetry algorithm, when implemented by one or more processors, can be device-agnostic and configure a VR device to be patient-centric/user-specific. In some implementations, the adaptive map perimetry algorithm accesses a normative dataset or database (e.g., referred to herein as the Envision normative dataset or database) and/or a normative model generated from the normative dataset or database. For example, the normative dataset or database may be implemented for (1) age-corrected mean normal fields, and (2) normative references for detection of VF locations with abnormally low visual sensitivities. An age-corrected spatial model can be generated for the normal hill of vision and/or normal isopter values.

Figure 4:
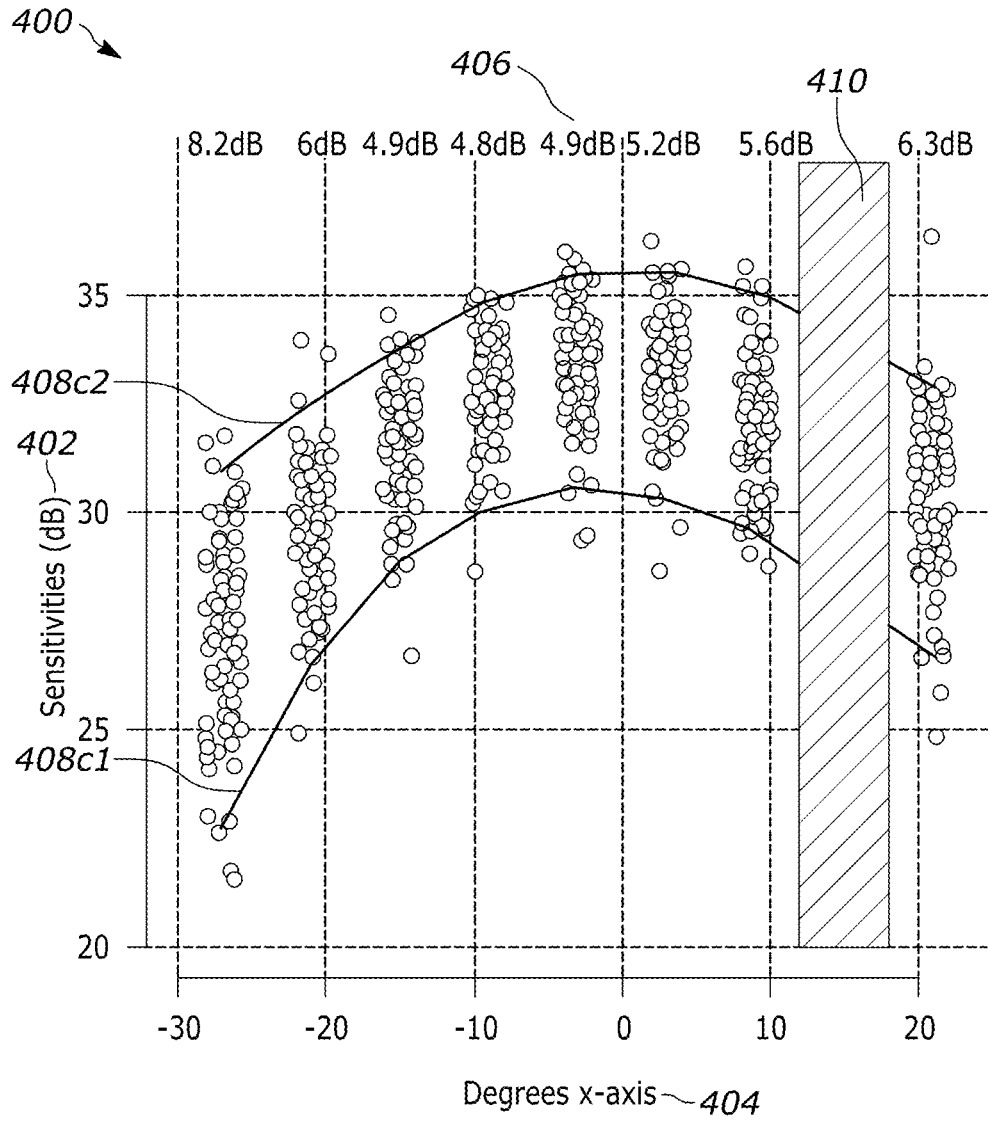
FIG. 4 illustrates a diagram of sensitivities (in dB) for given degrees of healthy eyes, in accordance with various embodiments of the present disclosure.

In some aspects, the model may use quantile surfaces and related values, which can provide normative references for the detection of anomalous VF locations. This approach can increase statistical power and avoid the limitations of empirical normative references used in conventional SAP. From the normative model, an individualized reference VF can be derived. The derivation of such reference VF is motivated by the fact that there is a lot of inter-individual differences in the overall sensitivity (the GH) and shape in the hill of vision among healthy eyes after correcting for age effects. As shown in FIG. 4 for 95% of healthy eyes, the sensitivity can vary by 5 dB to up to 8 dB (406) or even more due not only to ocular opacities (e.g., cataracts), but also attentional and criterion differences. The reference VF may be obtained by subtracting to the mean normal VF the difference in the GH for a user and the mean normal GH.

FIG. 4 shows example age-corrected sensitivities of trained healthy eyes. The data shown for FIG. 4 are from the SUNY-IU dataset. The x-axis (degrees 404) shows the horizontal degrees of visual angle. The y-axis (sensitivities (dBs) 402) shows the sensitivities for 91 healthy eyes of 91 subjects at y visual angle of 3°. The curves (408$cl$ and 408$c2$) show the 95% confidence intervals at each x-value across x-axis 404. The length of the intervals is shown in dB 406. The rectangular region 410 represents a blind spot.

The adaptive map perimetry algorithm can be implemented in accordance with such parameters or values. For example, the total deviation (TD) probability maps from the 24-2 can be used to identifying healthy regions of the VF, which can be used to run a fast (e.g., 10 presentations), simplified thresholding algorithm on 10 locations suitably selected from the healthy areas (e.g., the gray dots in FIG. 2A) to estimate the GH. The reference VF can be obtained as the age-corrected mean normal VF minus the difference in mean normal GH and the user's GH. This individualization via a reference VF is expected to increase the sensitivity of map perimetry.

In some implementations, a normative dataset or database can be used to determine the specificity at different suprathreshold levels. A function can be implemented to determine the suprathreshold level to use at any given specificity (e.g., 95%). In instances where no previous VF SAP data is available, a preliminary screening test with suprathreshold stimuli that at each location corresponds to percentiles (probability levels) of 0.05 and 0.01 according to Envision normative references can be performed. Such a screening procedure, for example, can be implemented as follows. At each location a stimulus corresponding to the percentile 0.05 can be presented or displayed (e.g., on a VR device). If it is seen or otherwise detected, then the adaptive map perimetry algorithm stops and the location will be flagged as healthy. If it is not seen, then a stimulus corresponding to percentile 0.01 will be presented or displayed (e.g., on VR device). If it is seen or otherwise detected, then the location will be assigned the probability level 0.05. If it is not seen or detected, then it will be assigned the probability level of 0.01. Such implementation provides a much more efficient and/or faster test than the thresholding algorithms of SAP.

The initial locations will then be obtained for the TD probability maps as described herein.

Figure 2A:
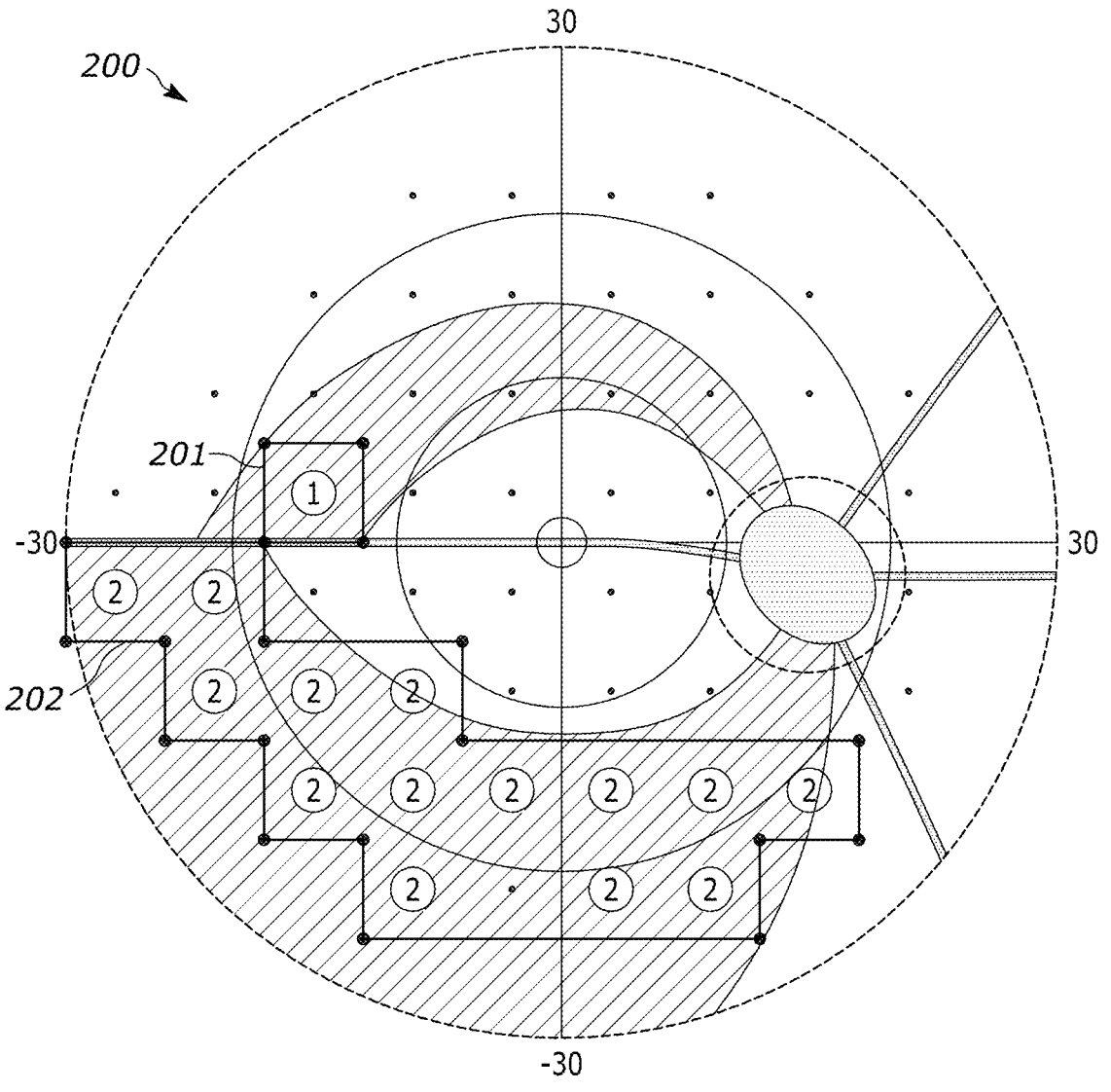
FIG. 2A illustrates an example spatial cluster analysis on defective locations from 24-2 conventional SAP to identify scotomata (identified by locations marked with "2" in the example) and their edges (black solid circles and connecting lines) that may be used or accessed by the example method of FIG. 1 or otherwise an adaptive map perimetry algorithm, in accordance with various embodiments of the present disclosure.
Figure 2B:
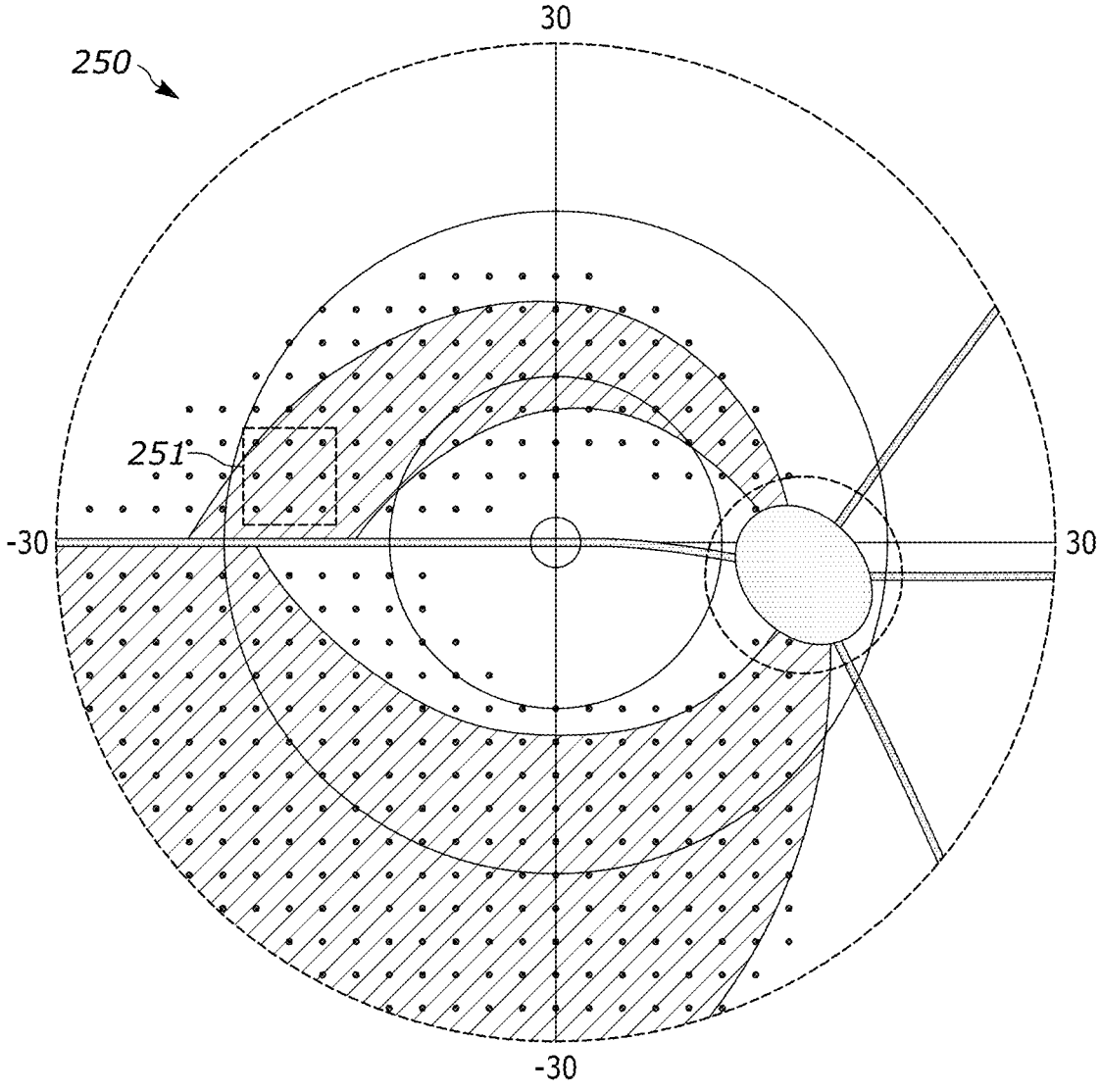
FIG. 2B shows the set of all possible test locations that can be selected for testing by the adaptive algorithm for a resolution of 2° horizontally and vertically between points.

FIG. 2A illustrates an example of spatial analysis to determine clusters of damaged locations. For the central +/−30° of the visual field 200 spatial analysis may be used to determine clusters of damaged locations, as described herein, e.g., for a specific VF test from a 24-2 pattern with defects. Such implementation can be carried out to determine starting locations for map perimetry as described herein. Such analysis and grouping can be applied or implemented, e.g., by the adaptive map perimetry algorithm, to map out scotomata using map perimetry. As shown for FIG. 2A, each of 2 clusters (e.g., cluster 201 defined by location(s) marked with "1" and cluster 202 defined by locations marked by "2") were fitted paths to their edges with the Jansonius structure-function map, leading to estimates of the shape and size of the 2 scotomata, in a fashion consistent with glaucoma pathophysiology. As shown in FIG. 2B, implementation of map perimetry can then be based on locations within the original estimate to confirm the defects seen in a 24-2 pattern inside the scotomata and test right outside of it to determine a more precise estimate of its shape than is possible with a conventional 24-2 pattern alone.

More generally, such computations can be implemented based on square grids with a specific resolution (e.g., 2° as in FIG. 2B). For example, a square grid portion 251 is illustrated for the square grid of FIG. 2B. In some implementations, a hull that envelops a given cluster may be set or pegged at half the resolution of a given square grid (e.g., square grid portion 251), which may be, e.g., a square area for cluster labelled "1" as shown for cluster 201 of FIG. 2A. Additionally, or alternatively, the edge locations or edges of a given cluster may be used determine the upper and lower edges of each scotoma. Still further, additionally, or alternatively, the cluster edges of one or more cluster may be used to fit Jansonius paths that envelop damaged locations of the eye (e.g., as shown for FIG. 2A).

Figure 3A:
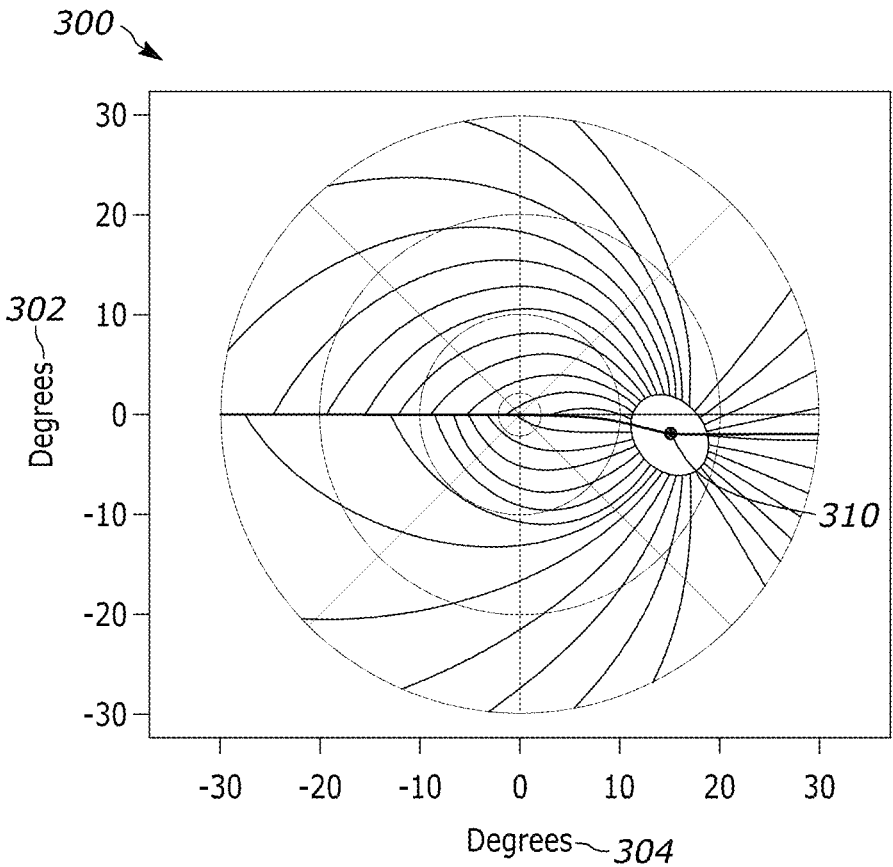
FIG. 3A shows an example implementation of a Jansonius map defined with respect to the center of the blind spot (dot 310), in accordance with various embodiments of the present disclosure.
Figure 3B:
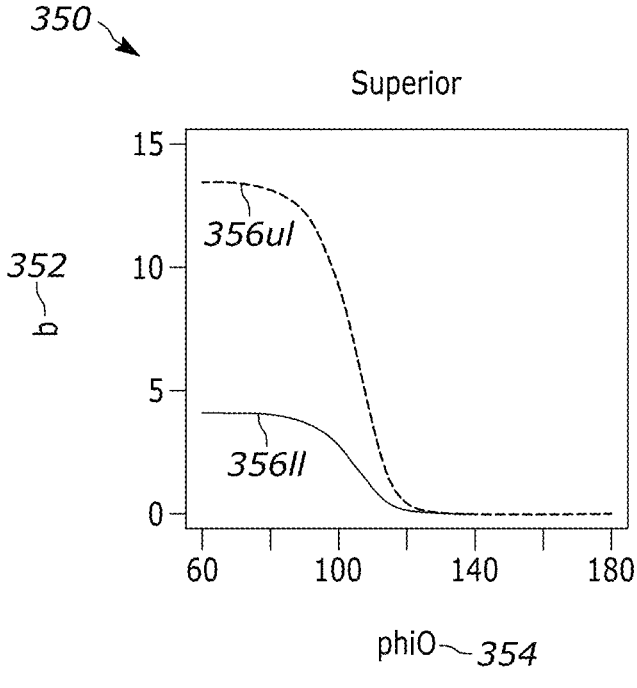
FIG. 3B illustrates an example of distribution values related to the Jansonius space of FIG. 3A, in accordance with various embodiments of the present disclosure.
Figure 3C:
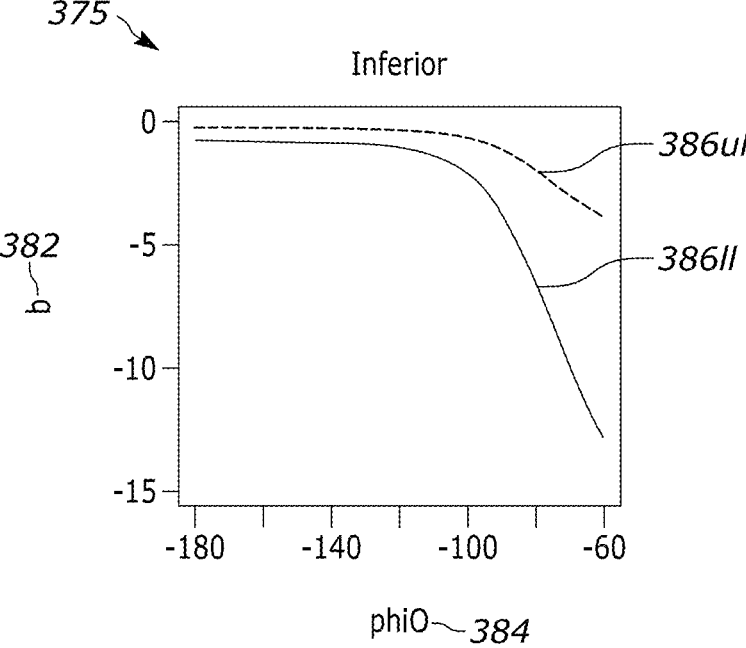
FIG. 3C illustrates a further example of distribution values related to the Jansonius space of FIG. 3A, in accordance with various embodiments of the present disclosure.

FIGS. 3A-3C refer to implementations regarding the Jansonius structure-function map. Generally, the Jansonius map describes mathematically retinal nerve fiber bundle trajectories with non-linear functions on a modified Euclidean space using sets of polar coordinates (r, $\varphi$), which is referred to herein as the Jansonius space. The equation used to describe the paths is as follows:

$$\varphi(r; \varphi_0) = \varphi_0 + b(r - r_0)^c \qquad (1)$$

In equation (1), $r_0$ is the radius of a circle for the starting point of the paths (interpreted as the optic nerve head, ONH, typically 4° of visual angle). $\varphi_0 = \varphi(r_0; \varphi_0)$ is the angular position of the trajectory at the starting point (interpreted as the angle of incidence on the ONH). Values b and c are parameters that depend on which region of the retina we are at (superior, inferior, temporal, nasal).

Once the (r, $\varphi$) duplets for a path with angle of incidence $\varphi_0$ are obtained, such values can be converted back to cartesian coordinates in the retinal space, which is flipped upside down with respect to the VF coordinates. The transformation between retinal space and Jansonius space depends on the position of the center of the blind spot (e.g., blind spot 310 as shown for FIG. 3A). For example, FIG. 3A shows the blind spot 310 at position (15, −2). Parameters b and c are dependent on the angle of incidence on the ONH $\varphi_0$.

The model may be implemented in any programming language, such as the R or the C# programming language, and can be depicted as shown for FIG. 3A. FIG. 3A comprises VF coordinates in degrees (e.g., having −30 to +30 degrees on x-axis 304 and −30 to +30 degrees on y-axis 302). The model provides support for map perimetry applied to glaucoma, in particular but not exclusively, wedge and arcuate scotomata. The model can be enhanced by through making it user-specific/patient-centric.

For each cluster of damaged locations, the values of the parameters b and c for the upper and lower edge bundles defining a scotoma are estimated by fitting equation (1) to the upper and lower cluster edge points as shown in FIG. 2A after converting their coordinates from the VF space to the Jansonius space. In one implementation, a patient's center position of the blind spot may be input into the transformation to the Jansonius space to adapt implementation to the user.

Additionally, or alternatively, other user-specific implementation can include updating or changing anatomical features, such as the angle of the temporal raphe and assumptions regarding how ganglion cell bundles travel throughout the retina.

After selecting starting locations from a pool of initial locations as, e.g., in FIG. 2 B, the scotoma estimates can be updated iteratively as part of the adaptive map perimetry. Each iteration may be as follows: present visual stimuli and record the results in the initial locations and once all results are gathered, perform the cluster analysis and fits with equation (1) to obtain updated scotoma estimates, modify the pool of possible test locations from such estimates, and select new untested locations. The adaptive algorithm may be repeated for each scotoma until the estimated scotoma does not change substantially with respect to the previous iteration, or all surrounding locations are deemed not damaged, or if the operator decides to interrupt the test and save results.

In some implementations, in order to avoid extreme and/or unstable fits, parameter b values can be algorithmically constrained to produce or output plausible values. A 95% distribution of values for parameter b can be determined as a function of do (i.e., phi0). FIGS. 3B and 3C illustrate this, with curves 356*ll* and 386*ll*, respectively, representing the lower limits and curves 356*ul* and 386*ul*, respectively, representing the upper limits for respective superior (FIG. 3B) and inferior (FIG. 3C) hemifields. Each of FIGS. 3B and 3C correspond to a hemifield, e.g., one of two halves of a sensory field of vision.

In both cases for FIGS. 3B and 3C, the upper limit (356*ul* and 386*ul*) can be calculated from the lower limit (356*ll* and 386*ll*) by multiplying the latter by the factor $e^{1.2}$.

The output of the fits from these functions can be obtained by implementing least squares. If the fit itself is unreliable (e.g., based on reliability criterion), then the average values for β can be used (e.g., −1.9 and 0.7 for superior and inferior hemifields, respectively).

Aspects Regarding the Adaptive Map Perimetry Algorithm

The disclosure herein provides implementations of device-agnostic software (e.g., the adaptive map perimetry algorithm) for implementing or executing clinical functional tests in head-mounted displays (e.g., VR devices). This section provides example implementations or aspects of the device-agnostic software (e.g., the adaptive map perimetry algorithm) and related devices, e.g., VR-devices.

Conventional SAP

Conventional SAP can be improved and automated with a Bayesian strategy (e.g., a ZEST algorithm implementation). Since the Swedish Interactive Threshold Algorithm (SITA) Standard remains a most commonly used conventional strategy, comparisons or improvements can be measured against it. Hardware differences between VR devices can be quantified to further measure differences between SITA and ZEST algorithms and their respective retest variabilities. Thresholding can be used to compare differences in hardware and settings for specific perimeters, such as starting locations.

Implementations may use or be based on a given background (e.g., 10 cd/m$^{-2}$), test locations, and test size (e.g., Goldmann Size III; 0.43° of diameter) for a given device, e.g., VR device.

Some aspects may include:
1. Output of the adaptive map perimetry algorithm can be comparable to a Humphrey Field Analyzer (HFA), and the limits of agreement are no greater than between HFA and any other commercial perimetric device.
2. Output of the ZEST algorithm is comparable to HFA with SITA Standard, e.g.:
   Test times are comparable (or shorter) for both healthy and glaucomatous eyes
   Retest variability is the same as or smaller than for HFA SITA Standard Envision's ZEST-Based Algorithm As described herein, an adaptive map perimetry may output from a ZEST algorithm. ZEST is a thresholding algorithm comparable to the SITA Standard. The adaptive map perimetry algorithm is a suprathreshold approach for measuring the extent and shape of scotomata, instead of the depth as ZEST or SITA try to do. Together, implementation of the adaptive map perimetry algorithm with the ZEST algorithm may be referred to herein as the Envision ZEST-based algorithm or Envision's ZEST algorithm.

Figure 5A:
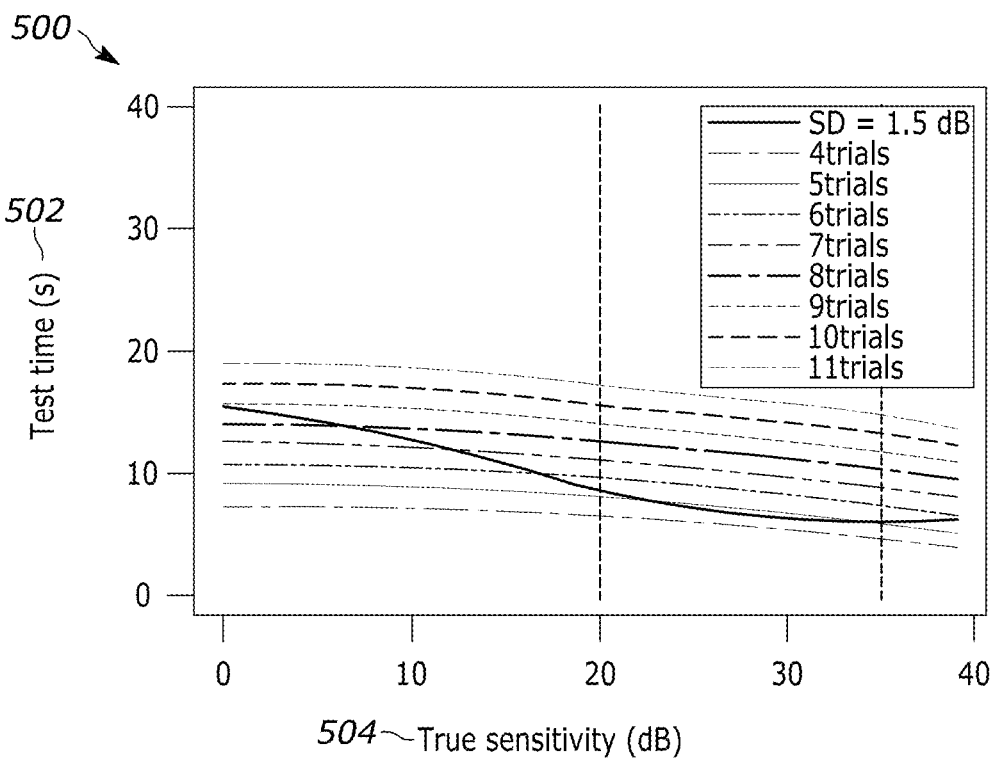
FIG. 5A illustrates a diagram illustrating test time (in seconds) over true sensitivity (in dB) over various tests comprising various trials, in accordance with various embodiments of the present disclosure.
Figure 5B:
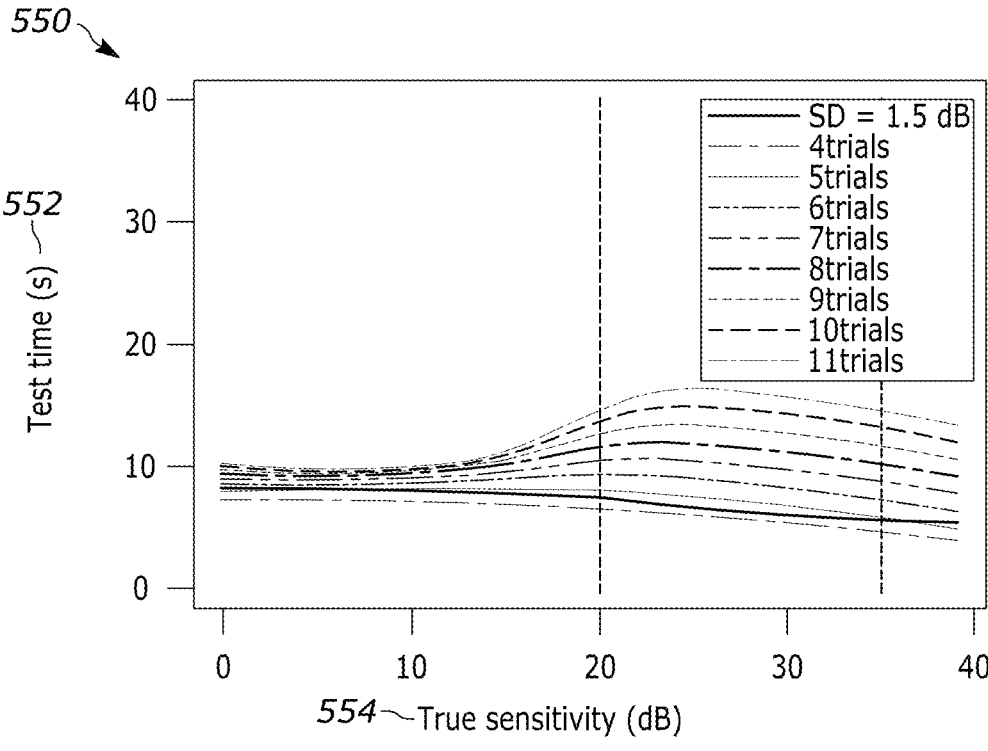
FIG. 5B illustrates a second diagram illustrating test time (in seconds) over true sensitivity (in dB) over various tests comprising various trials, in accordance with various embodiments of the present disclosure.

Additionally, or alternatively, in some implementations a portion of the HFA dynamic range may be used to implement testing in order to make testing shorter or otherwise more efficient. For example, as shown for each of FIGS. 5A and 5B, a range of 20 dB to 40 dB may be used. The values of the diagrams of each of FIGS. 5A and 5B are generated from simulations of testing time (502, 552) for each location with the ZEST and the full dynamic range (e.g., as shown for FIG. 5A across true sensitivity (dB) values 504) compared to the useful dynamic range (e.g., as shown for FIG. 5B across true sensitivity (dB) values 554). As shown, the true sensitivity values for each of FIGS. 5A and 5B (504 and 554, respectively) are the same or similar from a range of approximately 20 dB to 40 dB. Accordingly, limiting testing to within this range alone can improve efficiency or shorten testing by eliminating testing outside of this range. It is to be understood that the range may include extended, additional, and/or different values as well.

Normative Database

A normative database or otherwise normative dataset may be used to develop device-agnostic analytical methods for the ZEST algorithm, as well as by the adaptive map perimetry algorithm. A normative model may be constructed from the normative dataset that can be used for different hardware configurations and limitations after device-specific calibration. In some implementations, normative values may be implemented using quantile regression.

Some aspects may include:
1. Normative values may be generated using quantile regression.
2. The normative references can be modulated by external biometric measurements (e.g., refraction, axial length, corneal curvature, etc.) since statistical sensitivity to detection is expected to increase as more additional (independent) information is included.

3. A model (e.g., normative model) may also be developed for calibration of the normative references for use in different devices, keeping the software device-agnostic.

Progression Analysis

In some implementations, Permutation of Pointwise Linear Regression (PoPLR) may be implemented for the analysis of conventional SAP from ZEST testing. Permutation analysis of spatial damage progression may be implemented for the adaptive map perimetry algorithm.

Some aspects may include:

1. PoPLR is implemented for providing progression analysis that identifies or detects focal loss over a VF. This can provide increased sensitivity compared to global indices such as mean deviation (MD) and other sophisticated models of progression such as ANSWERS (Analysis with Non-Stationary Weibull Error Regression and Spatial Enhancement).

2. The output of a PoPLR implementation can provide increased sensitivity compared to other sophisticated, state-of-the-art models, such as ANSWERS.

Map Perimetry

In some implementations, the adaptive map perimetry algorithm can be implemented to provide a suprathreshold methodology for defining an extent of glaucoma scotomata, which can be an improvement over depth of defect of pre-determined locations (as, e.g., the 24-2 test). Implementing map perimetry may comprise determining starting test points. Such starting points may be based on or be obtained from previous perimetry tests, such as the 24-2, from OCT results, or by any other implementations (e.g., manual selection from fundus images) to obtain regions of interest or another 24-2 suprathreshold screening test. Implementing map perimetry may further comprise determining a reference VF, which can be obtained by direct estimation of the GH of the VF.

Some aspects of map perimetry may include:

1. Implementing and executing an individualized model based on a mathematical map (e.g., Jansonius map) of nerve fiber paths that can be used to describe the pathophysiology of glaucoma.

2. Map perimetry provides adaptive and self-correcting output because test locations are selected during run-time depending on the results and status of the test.

3. Map perimetry can be executed efficiently by a processor (e.g., of a VR device), as only relevant areas of the VF are tested, ignoring areas that do not have glaucomatous damaged.

4. Unlike any other perimetry method, map perimetry may use healthy regions of the retina as input to obtain a reference VF individualized for each patient.

5. Map perimetry is implemented as patient-centric, wherein a reference VF can be adjusted for each patient from normative data, therefore suprathreshold stimuli are individualized per subject. Further, an individualized model based on the Jansonius map can be used to describe scotomata is individualized for each patient.

6. Map perimetry can be used to derive important spatial metrics and characteristic of damage of the visual field alike to those from kinetic perimetry (e.g., such as sensitivity isopters and scotoma mapping).

7. Map perimetry eliminates three major limitations of traditional kinetic perimetry that are a direct consequence of it being manual, e.g., each of the following can be eliminated: high retest variability; high inter-operator differences; and/or lack of standardized analytical methods.

8. Analysis for map perimetry can be based on spatial and statistical methods that are novel in perimetry, e.g., the adaptive map perimetry algorithm.

9. Due to the shift from assessing depth of defect to assessing shape and extent of scotomata, structure-function correlations, as provided by map perimetry, are expected to be better than for conventional perimetry tests.

Implementation and Modeling

One or more processors may implement computing instructions that may comprise the software or algorithms (e.g., the adaptive map perimetry algorithm) as described herein. The one or more processors may be a processor of a headset device (e.g., such as a VR device) and/or a processor of computing device (e.g., a remote computing device) communicatively coupled (e.g., via a network) to the headset device and configured to send and receive data to and from the headset device.

In various implementations, visual stimulus, such as light stimulus, can be visualized or displayed on the headset device. Additionally, or alternatively, immersive multimedia images can also be visualized in a headset device. For example, immersive multimedia images are images obtained and/or generated for depicting or rendering on a display of a VR device. For example, the VR visualizations can be viewed by a user, such as a patient, via a VR device. In various embodiments, VR can refer to an immersive user experience, where the user can experience the sensation of a three-dimensional (3D) environment. For example, in one embodiment, the visualization of immersive multimedia image(s) can be used to create a real-world experience for a user, such as a patient. The immersive multimedia image(s) can direct a user to look, or move his or her eye(s), in certain directions in order to implement VF testing.

More generally, a headset device may comprise any computing device capable of visualizing or generating visual stimuli and/or immersive multimedia images to create a visual experience for the user. In some embodiments, for example, a headset device may be any commercial electronic display device with a display screen. In aspects where the headset device is a VR device, such VR device may comprise any one of a PICO device, a Google Cardboard device, a Google Daydream view device, an Apple Vision device, an Oculus Rift device, a PlayStation VR device, a Samsung Gear VR device, or an HTC VIVE device. Each of these electronic display devices may use one or more processors capable of visualizing light, visual stimulus, and/or immersive multimedia images in VR. For example, the Google Cardboard VR device includes a VR headset that uses one or more processors of an embedded smart phone, such as a smart phone, which, in some embodiments, can be a Google Android-based or Apple iOS-based smart phone, or other similar computing device, to visualize the immersive multimedia images in VR. Other VR devices, such as the Oculus Rift, may include a VR headset that uses one or more processors of a computing device, such a personal computer/laptop, for visualizing light, visual stimulus, and/or immersive multimedia images in VR. The personal computer/laptop may include one or more processors, one or more computer memories, and software or computer instructions for performing the visualizations, annotations, or transmission of light, visual stimuli, and/or immersive multimedia images or VR visualizations as described herein. Still further, other electronic display devices may include one or more processors as part of a headset that can operate independently from the processor(s) of a different computing device for the purpose of visualizing light, visual stimuli, and/or immersive multimedia images in VR. An electronic display device may also include software or computer instructions for capturing, generating, annotating, augmenting, transmitting, interacting with, or otherwise manipulating the such visualizations.

In some embodiments, the headsets of the VR devices can include focal distance lenses, such as 40 mm focal distance lenses, to focus a user's vision on a VR visualization, such as the exemplary VR visualization or image. For example, the distance from the VR headset housing to the screen interface, such as the screen interface of a smart phone in a Google Cardboard headset, as viewed through the focal distance lenses can create a VR experience for the user, such a patient.

In embodiments that do not implement VR, a display screen, such as a computer monitor, tablet screen, television screen, or other such screen may be used to render light, visual stimuli, and/or otherwise images and/or visuals, such as those described herein.

In various embodiments, the electronic display devices may include embedded sensors and/or cameras that track a user's head motions and adjust the viewpoint of the visualization to simulate an environment or otherwise visual field test area, giving the user the sensation that the user is looking around within a 3D world or otherwise test area. In some embodiments, the embedded sensors may be sensors associated with the mobile device or other computing device that is embedded in a headset of the electronic display device. In other embodiments, the sensors may be part of the electronic display device itself. In some aspects, the camera and/or sensor can take images of the user's eyes.

In various embodiments, an electronic display device can include or be communicatively coupled to input controls. For example, in some embodiments, the inputs control can be buttons located on a headset device. In other embodiments, the buttons can include magnets attached to the headset device's housing, where the magnets interact with a computing device embedded in the headset, such as a smart phone, to cause the computing device to sense (e.g., via a magnetometer located in the computing device) movements of the magnet when pressed, thereby acting as an input source for the headset device. In other embodiments the input controls may include separate joysticks or wired or wireless controllers that a user may manipulate by hand to control the headset device and/or visualizations of the headset device. Still further, in other embodiments, the headset device, or its associated smart phone or personal computer, may allow input commands via voice or body gestures to control the headset device and/or visualizations of the headset device.

In various embodiments, the input controls of a headset device allow a user to interact with a visualization, where the user, wearing a headset device can provide input to analyze, review, augment, annotate, or otherwise interact with a visualization. In some embodiments, a user may use the input controls to select from a menu or list displayed within the visualization as displayed by a display screen of the headset. For example, the displayed menu or list may include options to navigate or highlight certain views or features of the headset visualization. In other embodiments, graphics or items may be interactive or selectable with the headset visualization. Still further, in other embodiments, the user may provide textual, graphical, video or other input to the headset visualization in order to augment, or annotate the headset visualization. In some embodiments, augmentation or annotation of the headset visualization will cause the same augmentation or annotations to appear in the visualization (e.g., such as in the immersive multimedia image(s)), upon which the headset visualization is based, and/or vice versa. In various aspects, a user may be engaged in a VF test and may provide input via the input controls and/or display screen, in order to indicate when the see or otherwise detect a light stimulus, visualization, immersive multimedia image(s), and/or other displayed aspect or object rendered on the display screen. For example, in various aspects, the headset device or otherwise electronic display device may comprise a HFA device for measuring visual field of a user. In such aspects, a visual test may comprise a patient being instructed (e.g., by the headset device or otherwise electronic display device) to look at a central target. The user may then use an input control indicate when they see a visualization (e.g., light stimulus). Such visual field test can assess the user's retina's ability to detect a visualization or otherwise stimulus at specific points within the visual field.

In various embodiments, the input controls may be used with a crosshair or other indicator visible to the user within the headset visualization, such that the user hovering the crosshair or other indicator over a menu, list, graphic, text, video, or other item within the visualization can allow the user to interact with item, such as by clicking, pushing, or otherwise selecting the input control to confirm a selection or otherwise manipulate the item that the crosshair or other indicator is focused on.

In various embodiments, the visualization and/or immersive multimedia images and/may be submitted to a provider, such as a hospital or health services company, via a computer network. The computer network may be any computer network, such as the Internet (with or without the use of security protocols, such as Secured Sockets Layer and/or Transport Layer Security), a private network operated by the provider, or a secure virtual private network of the provider operated over the Internet. In some embodiments, a user, such as a patient or operator, may transmit immersive multimedia images and/or visualizations directly from a computing device, for example, a smart phone and/or electronic display device, which may have been used to capture or generate the immersive multimedia images visualizations, and/or related data, such as VF testing data.

In various embodiments, the immersive multimedia images may be saved in one or more memories of a computing device. For example, in some embodiments, the immersive multimedia images or videos may be saved in various image or video file formats, such as Joint Photographic Experts Group (JPEG), Portable Network Graphics (PNG), Tagged Image File Format (TIFF), bitmap (BMP), Moving Picture Experts Group (MPEG), or QuickTime (MOV).

Basic Settings

In some implementations, a 3D engine or model can be used to display the immersive multimedia images or videos on a display of a VR device or headset. For example, the UNITY engine or model may be used. The adaptive map perimetry algorithm may be implemented to configure the VR device or headset as device-agnostic. The adaptive map perimetry algorithm may load or implement device specific parameters or values defined in terms of physical and psychophysical units, such as visual angles, luminance in cd/m2, or the like. For example, in some implementations, a dB scale can be based on Weber contrast ratios or values and therefore allow for device-agnostic implementation, unlike for the HFA and any other commercial perimeters that use a device-dependent dB scale based on attenuation from maximum luminance differential. Still further, presentation of stimuli may be configured at infinity, so no lens correction or accommodation is needed unlike for the HFA to compensate for the fact that the stimuli are being presented on a display of a VR device, e.g., at 30 cm or less.

In various implementations, 3D modeling and/or RV techniques can be used to calculate visual angles in the x and y dimensions for each stimulus. For example, VR can be used to perform 3D modeling to calculate all the parameter similar to real world the size and location. A 3D to a 2D flat world image (e.g., an immersive multimedia image) can be fitted with the 3D parameters. The 3D parameters can be mapped on the virtual world to provide information and/or other visual aspects in immersive multimedia images as described herein.

In some implementations a virtual projector rotates to an angle in the x and y axes and visualizes or displays a stimulus at a distance that a user can visualize in the display of the VR device.

Some aspects may include:
1. Defining a virtual world using physical units (e.g., meters or degrees, but arbitrary units can also be used) and distances to replicate the real world in the virtual world (e.g., VR space). Such implementation reduces modeling and conversions from physical units (e.g., meters or degrees) to computational units (e.g., image pixel position in the screen). Further, such implementation makes the definition of the virtual world device agnostic because each device can render or model the same units on its own hardware, e.g., display.
2. Further, implementation of a virtual projector simplifies execution by the processor, as mathematical computation is reduced that reduces computational load, making the software operate efficiently and faster. Such implementation ensures that, as long as the setup and calibration data are correct, the stimulus is placed in the correct place, e.g., on a display of the VR device.

Other Forms of Perimetry

In some aspects, other forms of perimetry may be implemented. For example, the adaptive map perimetry algorithm can be customizable to replicate other types of perimetry, such as frequency doubling technology perimetry and SWAP, although no normative values are included for those. In some implementations, kinetic automated perimetry (with the same parameters as for the HFA and Octopus) may be implemented, but where no normative values are included. Still further, in some implementations, hybrid kinetic and/or static perimetry may be executed. Still further, in some implementations, visual stimuli can also be defined to be blur resistant.

Broader Impacts

The VR systems and methods described herein for glaucoma diagnosis and monitoring by adaptive VF analysis advance the health and welfare of the patients that use these innovations. This includes earlier detection and monitoring of the disease. Benefits include early detection of glaucoma and progression of glaucoma, for example, enabling earlier and more accurate detection of VF defects associated with glaucoma. The innovations described herein can identify and detect the disease at its earliest stages when intervention and treatment are most effective. This translates into improved visual outcomes and an enhanced quality of life for affected individuals.

Still further, the systems and methods described herein provided user-specific and/or personalized healthcare because the adaptive nature of our technology allows for personalized assessments of each patient's VF. By tailoring diagnostic and monitoring strategies to individual patient characteristics, including baseline VF data, the technology can help optimize patient care, helping inform treatment decisions.

Still further, the systems and methods described herein can reduce healthcare costs. Early glaucoma diagnosis and intervention can lead to reduced healthcare costs associated with the management of advanced glaucoma, including surgeries and costs associated with severe low vision.

Still further, the systems and methods described herein provide improvements to the field of eye disease and care, contributing to the scientific understanding of glaucoma, its progression, and the relationship between anatomical changes and functional deficits. This knowledge can drive further research and development in the field, potentially leading to breakthroughs in glaucoma management and other related eye conditions.

Still further, the systems and methods described herein can improve the quality of life by preserving vision is essential for maintaining overall quality of life, independence, and productivity. Patients with low vision have higher rates of depression and anxiety. By aiding in the early detection and management of glaucoma, the technology can help reduce the incidence of blindness.

Overall, there is significant potential for the technology described herein to have a positive impact on the health and welfare of patients.

Visual Field Feedback/Gamification

Visualization testing of the eye can be implemented by providing feedback to the test subject during an eye exam. Such implementation may be referred to herein as gamification. More generally, visual field testing is the examination process and protocol that involves the assessment of a test subject's, e.g., patient's, field of vision through presenting a stimulus in the test subjects' line of sight at varying levels of intensity. Conventionally, the process for visual functional testing can be error prone and depends on patient concentration. However, due to the difficulty in focusing the patient's eyes or otherwise attention, the test subject can lose concentration and reduce the efficacy of the testing results. In addition, the test subject does not get feedback during the test, which can and lead to inaccurate data collection, and therefore a failed visual field test altogether.

A computing system for visual field testing that incorporates visual field feedback (VFF) can include a device (e.g., a virtual reality (VR) headset) and/or one or more processor for providing feedback to the test subject to indicate their performance during the test. Such system is referred to herein as a VFF system. Visual field feedback, or otherwise feedback, can be provided to the test subject in response to input from the test subject after a presentation of a stimulus. For example, in visual field testing, the stimulus can take the form of varying visual objects that are presented to the test subject at varying light intensities. In various aspects, VFF can comprise feedback that is presented to a test subject during visual field testing and can take a form of one or more types of feedback, such as visual feedback, audio feedback, tactile feedback, haptic feedback, or a combination of types of feedback. In addition, the feedback can be used to test progress of the test subject, such as how much testing remains for a given vison field test. In this way, it is possible for the test subject to assess his or her test progress without assistance from the test administrator. It should be understood, however, that a test administrator (e.g., a medical professional) may administer the test without departing from the disclosure herein.

The illustrated VFF system and method may be used for visual field testing, including, by way of non-limiting example, rehabilitation from disease or injury, diagnostic and/or therapeutic purposes, visual performance enhancement, and/or visual function training.

In some aspects, feedback that is presented to a test subject (e.g., a patient) correlates to the accuracy of the test subjects' responses. In one example, if the test subject responds to a stimulus correctly, then positive feedback is can be generated. The positive feedback can be displayed (e.g., on VR headset). In addition, a cumulative amount or percentage of positive feedback can be tracked (e.g., stored in a computer memory).

Conversely, if the response is incorrect, then negative feedback can be generated and displayed (e.g., on a VR headset). In addition, a cumulative amount or percentage of negative feedback can be tracked (e.g., stored in a computer memory). In this way, feedback variation is result dependent. In various aspects, the VFF system is able to provide feedback in real-time or near-real-time, where the test subject is able to understand their performance when the VFF system outputs such feedback. In some aspects, a recognizable repetition and pattern of the feedback may be generated, e.g., based on the cumulative amount(s) and/or percentage(s) of positive and/or negative feedback. In some aspects, the cumulative amount(s) and/or percentage(s) of positive and/or negative feedback may be used to generate a score based on the amount of positive and/or negative feedback, and/or comparison thereto. In some aspects, the score may be displayed to the test subject in real-time or near real-time as the test subject engages in the visual field test. Still further, in some aspects, the cumulative amount(s) and/or percentage(s) of positive and/or negative feedback may be used to generate a graphical chart or image graphically depicting, e.g., to the test subject, the cumulative amount(s) and/or percentage(s) of positive and/or negative feedback. In some aspects, based on value of the cumulative amount(s) and/or percentage(s) of positive and/or negative feedback a specific graphic may be displayed (e.g., via the VR headset), where one graphic can be displayed for positive feedback or cumulative values thereof, and another graphic can be displayed for negative feedback and/or cumulative values thereof.

In some embodiments, an artificial intelligence model may be trained and executed to generate feedback based on responses given by the test subject. In such aspects, training data in the form of test subject responses from current or previous testing (e.g. technical feedback such as one or more button presses, eye-motion(s), and/or otherwise gesture(s) of the test subject) may be used to train the model for generating positive feedback and/or negative feedback. More generally, in various embodiments, a machine learning model may be trained using a supervised or unsupervised machine learning program or algorithm. The machine learning program or algorithm may employ a neural network, which may be a convolutional neural network, a deep learning neural network, or a combined learning module or program that learns in two or more features or feature datasets (e.g., response data of a plurality of users). The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. In some embodiments, the artificial intelligence and/or machine learning based algorithms may be included as a library or package executed on the one or more processor(s) as described herein. For example, libraries may include the TENSOR-FLOW based library, the PYTORCH library, and/or the SCIKIT-LEARN Python library.

Machine learning can involve identifying and recognizing patterns in existing data (e.g., such as training an artificial intelligence model based on feedback indication or responses of users as they use the system) in order to facilitate making predictions or identification for subsequent data (such as using the model on new response(s) of a new individual as input into the model in order to determine as output of the model a prediction or indication of feedback, e.g., predicted accuracy value corresponding to a percentage that a test subject correctly responded to displayed stimuli). As another example, training data may include feature data such as user responses including button presses (e.g., pressing buttons of a VR device), eye motion of the test subject away from a screen or to a specific area of a screen of a VR device, correct object identification within the VR device, or other action of the test subject. Additionally, or alternatively, feature data may also include spatial mapping data, which may comprise mappings of spatial patterns of damage of a user's (e.g., test subject's) eyes. The spatial mapping data can be used to approximate vision information, e.g., a field of view of the user, to define whether a user is expected to see out of a damaged and/or non-damaged area of the eye. The AI model may be trained with various spatial mapping data of a plurality of user's eyes against the label data (e.g., the test user's responses defining whether a user can see or detect a given stimulus). The output of the AI model can be an accuracy prediction based on the spatial mapping data and/or test responses. The output of the AI model can also be used to update the AI model.

Label data may include feedback given to the user (e.g., positive and/or negative feedback as described herein, which may include positive feedback indicating that the test subject correctly identifies the object with the VR device, negative feedback when the test subject incorrectly identifies the object with the VR device, negative feedback when the test subject's eyes move away from the VR device when the test subject should have otherwise provided a response but failed to do so, or other such feedback that indicates a negative or positive interaction of the test subject during the vision test.

Machine learning model(s), such as the visual field feedback testing model described herein for some embodiments, may be created and trained based upon example data (e.g., "training data" such as user response data) inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, patterns, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

In various aspects, the feedback (e.g., stimuli) presented to the test subject can be a recognizable reaction, change of environment, and/or an alteration of the test subject's field of few due to test subject interaction. Further, feedback can take any form, including visual, audio, tactile, or haptic feedback. Examples of visual feedback include shapes, images, video, color, light intensity changes. For example, this could be presented as a small, localized flash of color or imagery at the stimulus location (e.g., a location within or produced by the VFF system, such as display screen and/or speaker of the VR headset or device). Examples of audio stimuli include sound effects, music, and speech. For example, this could be presented as a low echoing sound effect. An example of haptic feedback is vibration or other physical sensation. For example, this could be presented as a mild, controlled vibration of the controller. In addition, the feedback can be formatted into a data format, such as a normalized data format, which can be stored on a server and provided to a test subject on a computer network.

Figure 6:
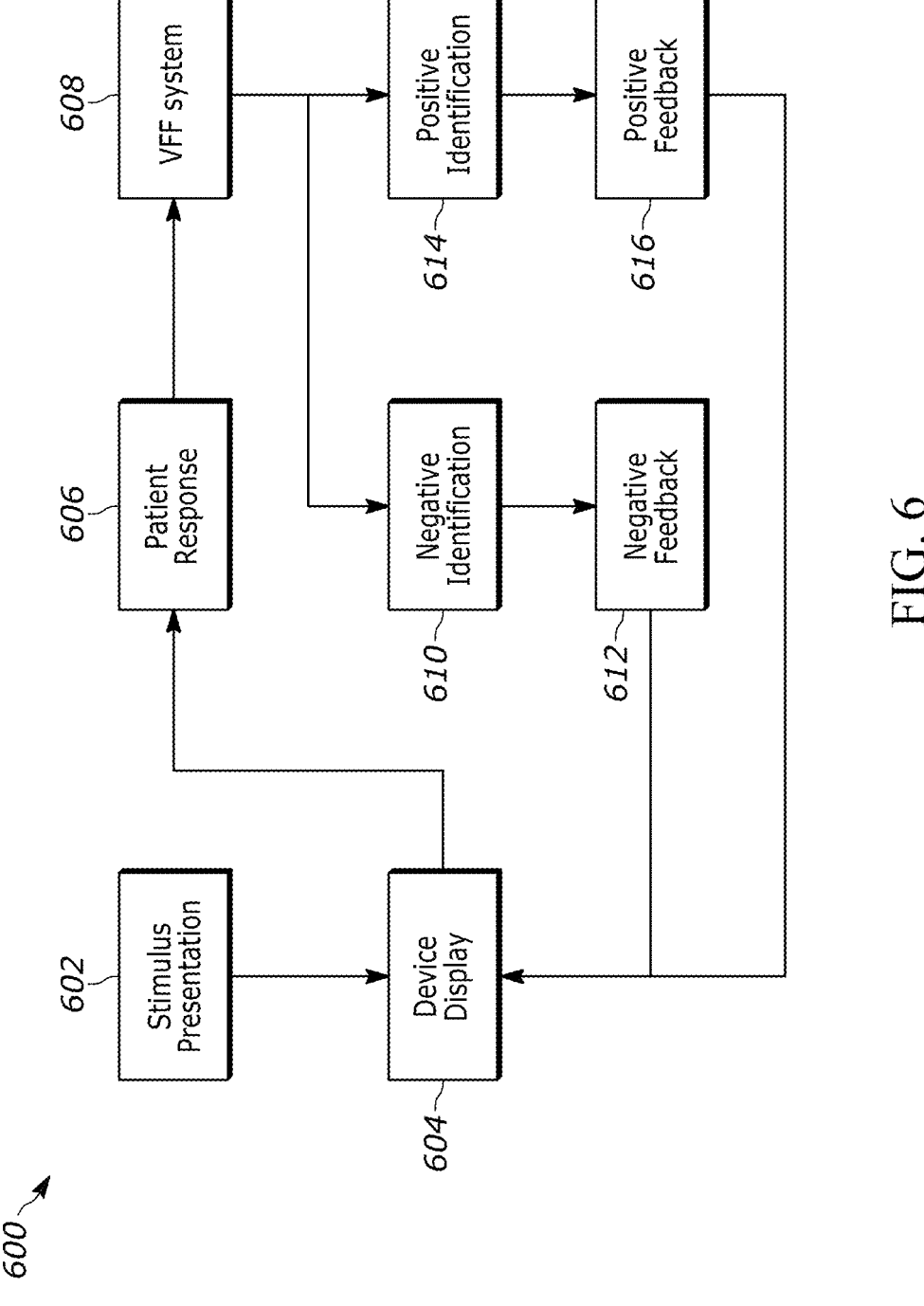
FIG. 6 illustrates a flow chart for presenting feedback in conjunction with performing a visual field test using visual field feedback in accordance with various embodiments of the present disclosure.

FIG. 6 illustrates a flow chart 600 for presenting feedback in conjunction with performing a visual field test using visual field feedback in accordance with various embodiments of the present disclosure. For example, FIG. 6 presents an illustrative implementation of an algorithm executing on a VFF system (block 608) in accordance with performing a visual field test. As illustrated for flow chart 600, a stimulus (block 602) can be rendered on the device display (e.g., a VR headset display) (block 604) and the test subject can respond (block 606) to the presented stimulus. The response can take the form of the test subject indicating they have recognized or otherwise acknowledged the stimulus presentation via an interaction with a designated controller (e.g., a designated controller of the display device 604). The response can also take the form of indicating that the test subject has not recognized the stimulus by no interaction with the controller. The VFF system then records and identifies whether the response is a negative identification (block 610) or positive identification (block 614) of the presented stimulus. Examples of data gathered by the test are listed below, but other data may be collected as available and appropriate. The VFF system can then provide a visual, audio, or haptic response (e.g., negative feedback and/or positive feedback) to the test subject. For example, if the identification is negative, then negative feedback (block 612) is delivered to the test subject. If the identification is positive, then positive feedback (block 614) is delivered to the test subject. For example, in FIG. 6, the feedback can be a positive or negative sound. If there is more to complete in the visual test, then the process can revert to the beginning block of presenting a stimulus to the test subject.

Feedback of a given test subject (e.g., a patient) that is recorded and interpreted by the VFF system can include, but is not limited to, the following data: (a) if the test subject (e.g. patient) response is a hit or miss; (b) the response time of the test subject (e.g. patient); (c) the location of the stimulus; (d) the gaze position of the test subject (e.g. patient); (e) eye movement of the test subject; (f) Time-of-Response (e.g., time of response of the VFF system).

The accuracy of the test subject's response can also be determined by analyzing the response as listed above and comparing it to either the actual location of the stimulus or a predicted response. The predicted response can be generated using an artificial intelligence model that is trained on response data from the current test subject or other test subjects and/or related feedback and/or indications, for example, as described herein.

For example, as shown for block 602, a stimulus is presented to the patient using the device display (e.g., a VR headset). For example, the stimulus can take the form of varying visual objects that are presented to the test subject at varying light intensities.

Further, at block 604, one or more processors can be used as part of a device display to present the stimulus to the patient. For example, the device display can be a VR headset, a computer or tablet screen, or other type of display.

At block 606, one or more processors may be configured to receive the patient response. The response can take the form of the test subject indicating they have recognized and acknowledged the stimulus presentation via an interaction with a designated controller. The response can also take the form of indicating that the test subject has not recognized the stimulus by no interaction with the controller.

At block 608, the one or more processors may be configured to, as part of the VFF system, record and identify the response as a negative response (block 610) or positive response (block 612).

At block 612, the one or more processors may be configured to present negative feedback to the patient. At block 614, the one or more processors may be configured to present positive feedback to the patient. For example, the feedback can include visual feedback, audio feedback, haptic feedback, or tactile feedback.

If there is more testing required, the algorithm of flowchart 600 can then implement a new session by returning implementation to block 604 to present the next stimulus to the patient. If there is no more testing required, the method ends and the test is finished.

Figure 7:
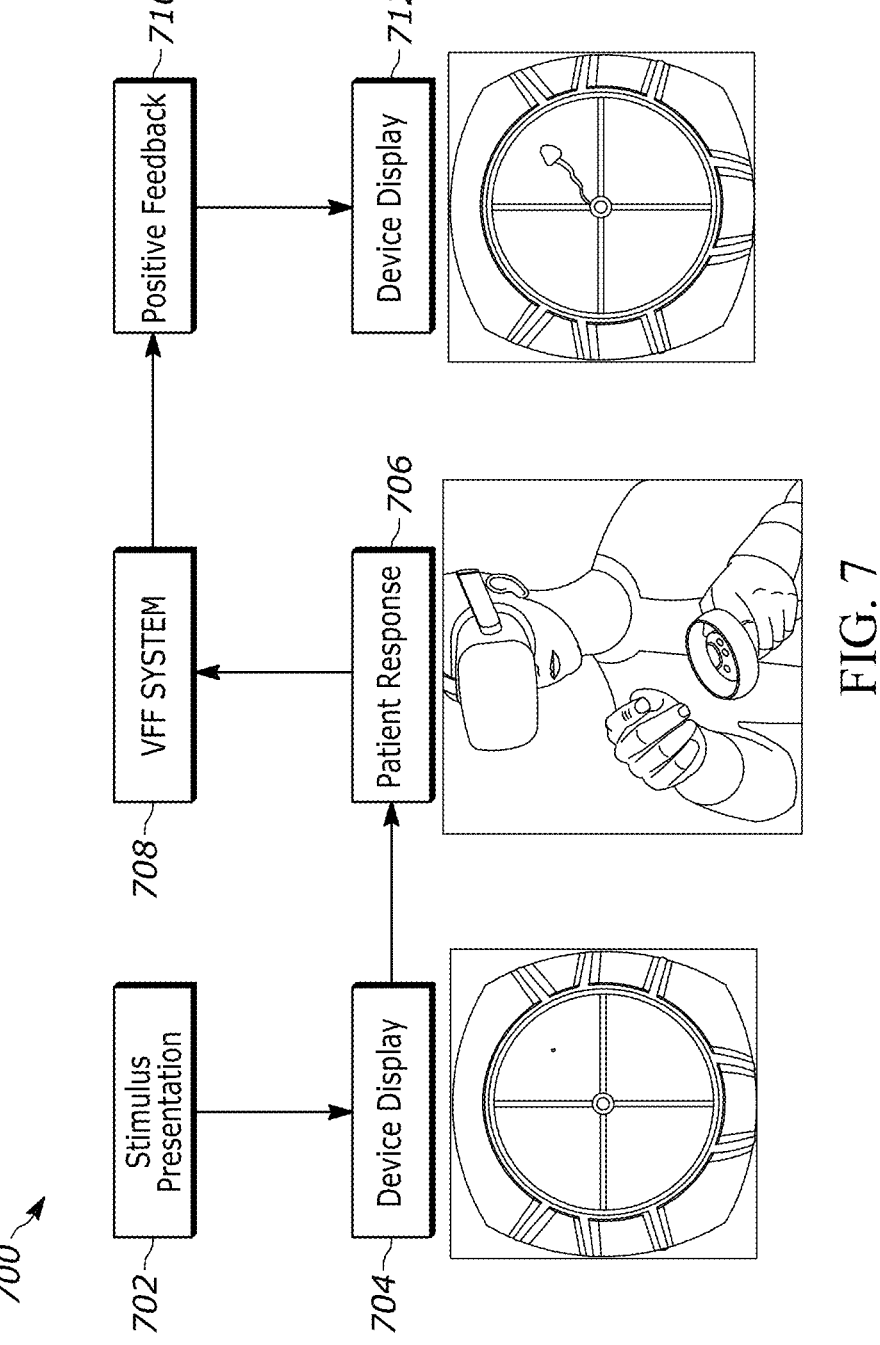
FIG. 7 illustrates an example implementation of the VFF system when operated by a user in accordance with various embodiments herein.

FIG. 7 illustrates an example implementation 700 of the VFF system when operated by a user in accordance with various embodiments herein. For example, FIG. 7 presents an illustrative implementation of the use of the VFF system where the feedback is both audio and visual. In some aspects, as shown for FIG. 7, the feedback is positive and consists of both a sound corresponding to a correct response and a visual representation of the patient response. In some aspects, the visual representation can be color coded to indicate a correct response and/or an incorrect response. For example, as shown for block 702, a stimulus is presented to a patient. The stimulus can be any one or more stimuli as described herein.

Further, at block 704, one or more processors can be used as part of a device display to present the stimulus to the patient. For example, the device display can be a display of a VR headset, a computer or tablet screen, or other type of display. The one or more processors may be processors of the VR headset itself and/or of a computing device communicatively coupled to the VR headset.

At block 706, the one or more processors may be configured to record the patient response to the displayed stimulus. The patient response can be recorded using by collecting input of the user, such as an input device, tracking the patient's head position or gaze, or other input collected and recorded for the patient's response to the stimulus.

At block 708, the one or more processors may be configured to, as part of the VFF system, record and identify the response, e.g., where recording may occur in a computer memory. In such aspects, the response can be identified as a positive response, which can include the patient correctly identifying an object presented on the display.

At block 710, the one or more processors may be configured to determine that positive feedback should be presented to the patient. The positive feedback may comprise feedback as described herein.

At block 712, the one or more processors may be configured to deliver the positive feedback to the patient. The form of the feedback may be any feedback or indication as described herein.

FIG. 8 illustrates an example visual field feedback (VFF) method 800 for automatically assessing visual field testing in accordance with various embodiments herein. For example, as shown for block 810 of method 800, one or more processors may be configured to display, on a headset device (e.g., a virtual reality (VR) device), a stimulus to a test subject (e.g., patient). For example, the one or more processors may be the one or more processors of a VFF system, as described herein, or it may be one or more processor of a personal computing device or other similar processing device.

Still further, at block 820, method 800 comprises recording, by one or more processors, a test subject's response to the displayed stimulus. For example, in some aspects, the test subject's response can include recognizing and acknowledging the stimulus via interaction with a controller or not recognizing or acknowledging the stimulus by not interacting with the controller. Further, the test subject's response can include (a) whether the test subject (e.g., patient) response is a hit or miss; (b) a response time of the test subject (e.g. patient); (c) a location of the stimulus; (d) a gaze position of the test subject (e.g. patient); (e) an eye movement of the test subject; (f) a Time-of-Response (e.g., time of response of the VFF system).

Still further, at block 830, method 800 comprises analyzing, by a Visual Field Feedback system (e.g., which may comprise a VR headset), a test subject's response to the displayed stimulus using a stimulus location. For example, the test subject's response can be analyzed based on the location of the displayed stimulus and can be input into an AI model executing on the more or more processors. The AI model can be trained with training data comprising response feedback of test subjects (e.g., button presses, eye-motion, or other such feedback provided by the user including as described herein), wherein the AI model is configured to output a prediction defining an accuracy value corresponding to a percentage that the test subject correctly responded to the displayed stimulus. The AI model can generate, based on the prediction defining the accuracy value, the feedback to the test subject.

Still further, at block 840, method 800 comprises providing feedback to the test subject based on the response and analysis. For example, the feedback can be positive or negative as described herein. Further, the feedback can include any of visual, audio, tactile, or haptic feedback. In another example, the feedback can be correlated to accuracy of the responses of the test subject. In another example, positive feedback is displayed if the test subject responds correctly and negative feedback is displayed if the test subject responds incorrectly. In another example, the feedback is formatted into a format that can be stored on a server and provided a test subject over a computer network as described herein.

The illustrated VFF method may be used for any of visual field testing, rehabilitation from disease or injury, diagnostic and/or therapeutic purposes, visual performance enhancement, or visual function training.

FIG. 9 illustrates a further example VF analysis method 900 for glaucoma diagnosis and monitoring by implementing adaptive map perimetry and, optionally performing visual field testing in in accordance with various embodiments herein. Method 900 may be implemented, for example, on one or more processor(s) as described herein. This could include one or more processor(s) of a VR headset and/or otherwise a computing device communicatively coupled to the VR headset. The disclosure herein applies with respect to the disclosure of FIG. 9.

With reference to FIG. 9, at block 910 method 900 comprises implementing a VF test on a display screen of an electronic display screen device (e.g., a virtual reality (VR) device). As described herein, the electronic display screen device may comprise a display screen positioned proximate to, or within a viewable distance from, a user's eyes, the electronic display screen device communicatively coupled to one or more processors. Still further, the VF test may be adapted to fit an area of the display screen based on values in a normative database or model, wherein the VF test is rendered as a same or similar visualization compared to one or more different electronic display screen devices having different display screens having different respective shapes, formats, sizes, and/or resolutions, wherein an adaptive map perimetry algorithm is configured to access or implement the normative database or model to adapt the electronic display screen device to be device-agnostic with respect to the one or more differently configured electronic display screen devices.

At block 920 method 900 comprises receiving visual test data indicating a visual field of the user.

At block 930 method 900 comprises detecting, based on the visual test data, one or more initial test locations specific to the user, the one or more initial test locations defining one or more healthy clusters indicative of an absence of scotoma and one or more damaged clusters indicative of scotoma.

At block 940 method 900 comprises generating, based on the one or more initial test locations, a spatial mapping identifying locations of the one or more damaged clusters.

Optionally, method 900 comprises blocks 950-980.

At block 950 method 900 comprises displaying, on a headset device (e.g., a virtual reality (VR) device), a stimulus to a test subject (e.g., patient).

At block 960 method 900 comprises recording, by one or more processors, a test subject's response to the displayed stimulus.

At block 970 method 900 comprises analyzing, by a Visual Field Feedback system (e.g., the VR device), a test subject's response to the displayed stimulus using a stimulus location and/or the spatial mapping. For example, the stimulus location may be a location within or produced by the VFF system, such as display screen and/or speaker of the VR headset or device. Examples of a stimulus (e.g., feedback) may comprise as a small, localized flash of color or imagery at the stimulus location. Examples of audio stimuli include sound effects, music, and speech. For example, this could be presented as a low echoing sound effect. An example of haptic stimulus (e.g., feedback) is vibration or other physical sensation. For example, this could be presented as a mild, controlled vibration of the controller. In addition, such feedback can be formatted into a data format, such as a normalized data format, that can be stored on a server and provided to a test subject on a computer network.

The spatial mapping may comprise, as described herein, mappings of spatial patterns of damage of a user's (e.g., test subject's) eyes. The spatial mapping may have been generated by an adaptive map perimetry algorithm using anatomical models of retinal nerve trajectories (e.g., a Jansonius map) and glaucoma pathophysiology to adapt itself depending on the patient's responses during runtime.

Analysis of the test subject's response comprises displaying one or more stimuli at field(s) of view of the test subject that are impaired as determined based on the spatial mapping. The analysis may comprise confirming spatial mapping based on the user's test responses. For example, an initial spatial mapping may be generated for the test subject using the algorithms or otherwise methods as describe herein. A stimuli may then be displayed in a field of view predicted to be impaired, blurred, or otherwise non-visible to the test subject based on analysis of the initial spatial mapping. The user can provide a test response (or fail to provide such a response). In instances where the user fails to respond, then the initial spatial mapping, or meta data related thereto, can be updated to create an enhanced spatial mapping confirming the test subject's damaged area(s) of the user eye related to the field of view. However, in instances where the user successfully responds, then the initial spatial mapping, or meta data related thereto, can be updated to create an enhanced spatial mapping confirming the test subject's non-damaged area(s) of the user eye related to the field of view. In the event that the user responds or does not respect to when he or she is expected to respond (based on the initial spatial mapping and the user's expected field of view therefrom), the initial spatial mapping (or a further updated version or meta data thereof) may be updated to reflect the possibility of damage or non-damage to the user's eye, as the case may be.

At block 980 method 900 comprises providing feedback to the test subject based on the response and analysis.

Asymmetries in the Shape of the Hill of Vision

Differences in the shape of the hill of vision within individual subjects produce varying asymmetries, most notably nasally between individuals. Assessment of the superior vs inferior and nasal vs temporal asymmetries with respect to the sensitivities for a 75 year old mean normal eye by computing the superior vs inferior differences in slopes and mean normal values as well as the nasal vs temporal demonstrate asymmetries that are subtle and non-significant. Linear regression of the changes of slope as a function of eccentricity in superior-inferior differences produce a change of −0.006 (dB/decade)/degree or −0.1 dB/decade from the macula to the periphery. Temporal-nasal differences in slopes are similar (−0.09 dB/decade from the macula to the periphery). Superior/inferior (SI) and nasal/temporal (NT) asymmetries in mean sensitivities are both statistically significant, with slopes of −0.12 dB for superior/inferior and temporal/nasal, or about a −2 dB difference.

The presence of the asymmetries make it difficult to properly model and analyze stimulus responses from a test subject. To account for this the asymmetries can be modeled and accounted for during testing. The shape of the hill of vision is generally not linear with sensitivities decreasing with eccentricity on average using all locations. This simple fit reasonably describes the average eccentricity effect, with a maximum difference between the mean eccentricity and a fitted eccentricity of less than 0.4 dB. However, due to asymmetries, the fit is not good enough, with differences of up to 2.1 dB. The average eccentricity model to obtain average sensitivities s as a function of eccentricity is $s = 33.5 - 0.35\ e + 0.013\ e^2 - 0.00039\ e^3$.

A more sophisticated model may account for each eye quadrant separately. In particular, to account for differences in the quadrants, the residuals (sensitivities at each eccentricity minus the cubit fit) are computed and a quadratic function is fit to those residuals. The values of the coefficients at each quadrant are then added to the average fit to give a distinct fits at each quadrant:

$$\text{Quadrant 1 } (x > 0, y > 0): s = 34.1 - 0.59e + 0.020e^2 - 0.00039e^3,$$

$$\text{Quadrant 2 } (x < 0, y > 0): s = 34.2 - 0.46e + 0.014e^2 - 0.00039e^3,$$

$$\text{Quadrant 3 } (x < 0, y < 0): s = 33.1 - 0.18e + 0.007e^2 - 0.00039e^3,$$

$$\text{Quadrant 4 } (x < 0, y > 0): s = 33.7 - 0.40e + 0.016e^2 - 0.00039e^3.$$

However, this approach still produces problems. Specifically, the superior and inferior modelling predict mean normal foveal sensitivity that are up to 1 dB apart and to obtain a single model of the visual field the quadrant models need to be stitched together. Another issue is that, even though considering age slopes alone looks to produce no issue, the fits for mean normal sensitivities from a 50 year old to a 100 year old vary considerably, so age must be considered.

Another possible approach to modeling the asymmetries is to use polar coordinates from −180° to 180° and capture the asymmetries once the age has been set. This model also includes age and the effect of age and eccentricity. The model for age-corrected mean sensitivities for a subject aged a years at a location with eccentricity r and at an angle θ in radians is:

$$s = 38.3 - 0.068a - 0.35r + 0.014r^2 - 0.00042r^3 -$$

$$0.063r\sin\theta + 0.039r\cos2\theta - 0.00058r^2\sin2\theta - 1.23\ 10^{-6}r^4\cos4\theta$$

There was no systematic or automatic approach to decide on this fit. Age and eccentricity are obvious choices given that sensitivity decreases with both age and eccentricity and age effect is more severe with eccentricity. Polynomials of 3rd order were selected for eccentricity because the hill of vision is known to have two inflection points. Trigonometric functions (e.g., Zernike-like polynomials) are included to account for the asymmetries in the hill of vision.

However, this model has an issue in that the intercept is too large (e.g., 38.3 dB).

Instead what is needed is an improved Visual field analysis (VFA) system that can model the HoV and the asymmetries in steps (e.g., by first fitting the age effect, then fitting the overall (symmetric) shape of the hill of vision, and finally, the asymmetries using Zernike-like polynomials.

Visual Field Analysis (VFA) System

With reference now to FIG. 10A, a VFA system 1000 for generating an improved individualized model of the HoV is shown. The VFA system 1000 includes a computing system 1002 and a headset device 1004. The computing system 1002 includes at least one processor 1005 and a memory 1006 that stores an average hill of vision (HoV) model and instructions that are executable by the at least one processor 1005 to perform various methods described herein. The headset device 1004 may include one or more of the various display systems described herein such as the device displays described in connection with FIGS. 6 and 7.

In operation, the computing system 1002 generates an eye difference estimate for a test subject relative to reference data for an average healthy eye obtained from a normative dataset. The eye difference estimate indicates a difference in overall sensitivity or general height (GH) and a rate of sensitivity decay with eccentricity (distance from the fovea) relative to the reference data. The computing system 1002 generates an individualized HoV model based on the eye difference estimate and the average HoV model 1008. As described in more detail below, the individualized HoV model incorporates individualized GH and eccentricity parameters to the average HoV model 1008. In particular, the individual eccentricity component is defined the so that its slope effectively captures differences from the age-corrected mean normal visual field. This definition enables a negative GH to represent below mean normal overall sensitivity and a positive GH to represent above mean normal overall sensitivity. Additionally, a negative eccentricity slope represents a HoV that is steeper than mean normal and a positive eccentricity slope represents a HoV that is shallower than mean normal.

The computing system 1002 initiates display of stimuli on the headset device 1004. In particular, the headset device 1004 displays a respective stimulus at a plurality of test locations. The computing system 1002 receives responses to each respective stimulus from a test subject that is wearing the headset device 1004 and stores the responses in the memory 1006.

The computing system 1002 analyzes the responses to determine a respective sensitivity value for the test subject at each of the plurality of test locations and determines total-deviation values for the test subject by subtracting the respective sensitivity value for each of the plurality of test locations from a corresponding value of the individualized HoV model. The computing system 1002 may additionally analyze the total-deviation values and provide feedback to the test subject based on the analysis.

The individualized HoV model generated by the computing system 1002 may also be used to readjust the reference visual field used for on the headset device 1004. For example, derivation of suprathreshold values as described herein my first be based on the average HoV and as testing with the VFA system 1000 progresses these values may be substituted for a best guess of the individualized HoV. The individualized HoV may also be used to assess whether some of the test locations should be retested using different suprathreshold values after estimating the eye's reference visual field to confirm damage (e.g., if it turns out that whole HoV is very depressed, which can be a consequence of cataract, etc). The individualized HoV may also be used to infer confidence intervals for the individual GH and eccentricity effects and individualized normative values from these individual GH. The individualized HoV model may also be the reference for spatio-statistical analysis of the testing results. The individualized HoV model may also be used to calculate normative references that are better founded mathematically computing quantile surfaces for the detection of abnormal test locations. These normative references can work for any custom grid, so long as locations in the grid are within the central 30° of the visual field.

The computing system 1002 may employ different processes for generating the eye difference estimate as described above. For example, the computing system 1002 may first determine a set of preliminary test locations and display, on the headset device 1004, a visual psychophysics algorithm (e.g., Staircase, Full Threshold, ZEST, etc.) at the set of preliminary test location to obtain preliminary sensitivities Then, the computing system 1002 may determine the overall sensitivity or GH and the rate of sensitivity decay with eccentricity of the eye difference estimate based on the preliminary sensitivities.

In other embodiments, the computing system 1002 may generate initial estimates of the overall sensitivity or GH and the rate of sensitivity decay with eccentricity and obtain interim responses of the test subject to the respective stimulus displayed at the plurality of test locations. The computing system 1002 may then analyze the interim responses to adjust the initial estimates of the overall sensitivity or GH and the rate of sensitivity decay with eccentricity and obtain confidence intervals and adjust levels of the respective stimulus displayed on the headset device based on the adjusted initial estimates to obtain respective sensitivity value for the test subject at each of the plurality of test locations. Then, the computing system 1002 may determine the overall sensitivity or GH and the rate of sensitivity decay with eccentricity of the eye difference estimate based on the respective sensitivity value for the test subject at each of the plurality of test locations. The initial estimates may include one or more of age-corrected mean normal values, values generated from analysis of one or more previous visual field tests, or values from a preliminary test administered to the test subject.

In some embodiments, the responses of the test subject to the respective stimulus displayed at the plurality of test locations on the headset device 1004 are a visual field. In these embodiments, the computing system 1002 may generate the eye difference estimate by identifying points in the visual field that are damaged, removing the damaged points from the visual field, and analyzing the remaining points within the visual field to generate the eye difference estimate and fit the individualized HoV model.

Figure 10B:
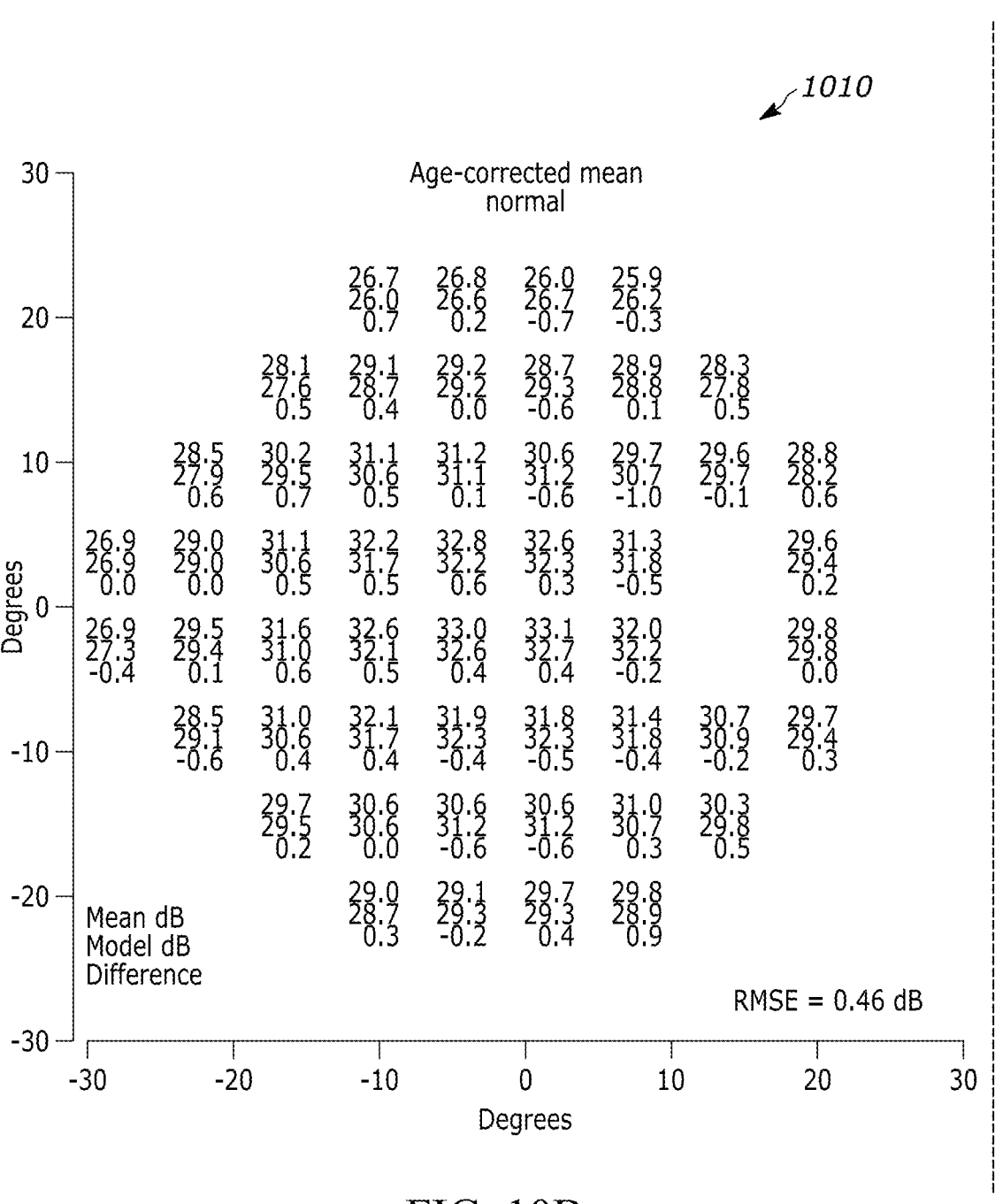
FIG. 10B illustrates an example average hill of vision (HoV) model, used in accordance with various embodiments herein, relative to an age corrected mean normal vision model.
Figure 10B:
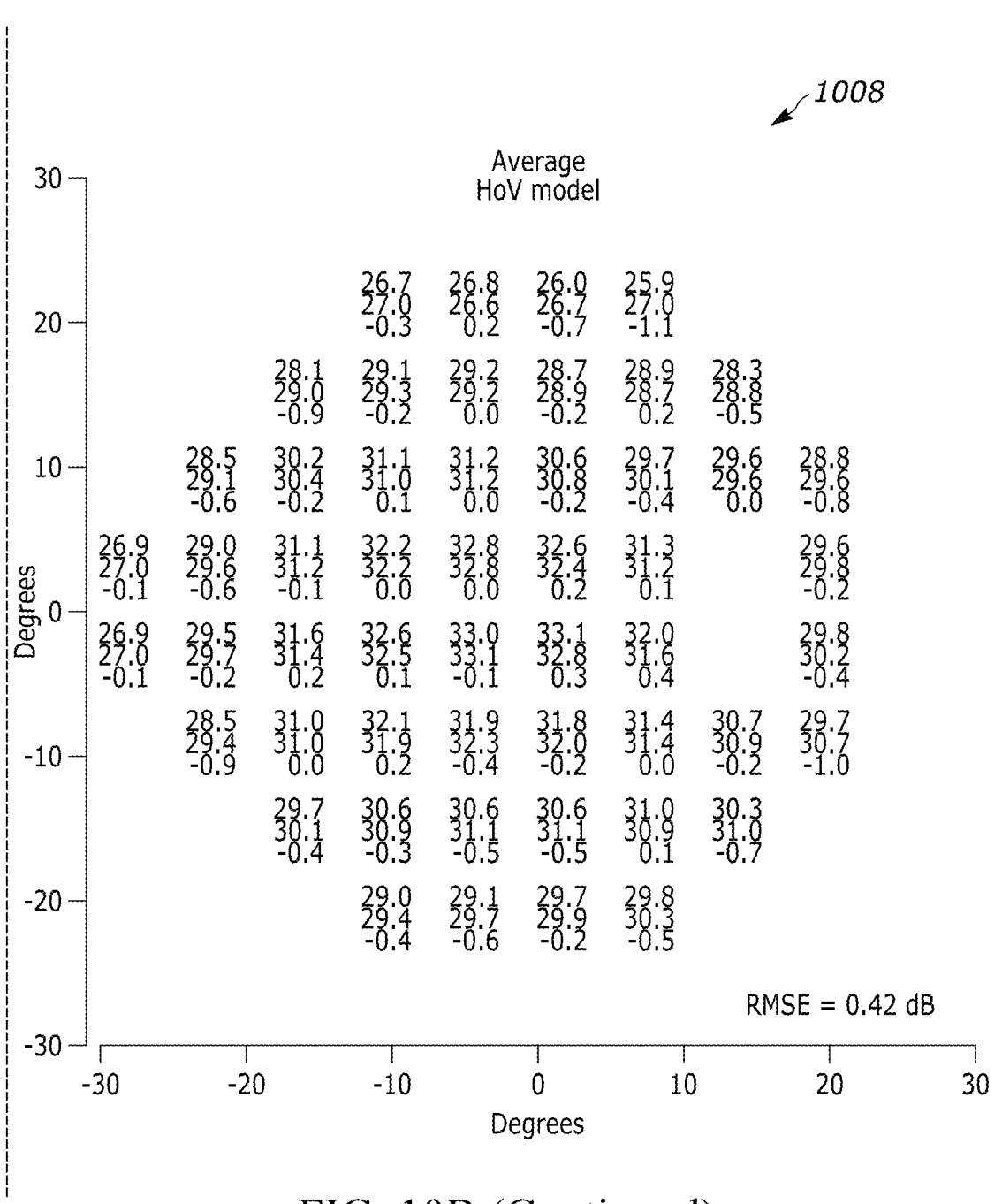

With reference now to FIG. 10B, one example of the average HoV model 1008 is shown in a graphical representation next to a graphical representation of an age corrected mean normal vision model 1010. As shown in FIG. 10B, the average HoV model 1008 has a lower Root Mean Square Error (RMSE) than the age corrected mean normal vision model 1010 and the greatest differences between the average HoV model 1008 the age corrected mean normal vision model 1010 occur at rim or perimeter locations.

Figure 10C:
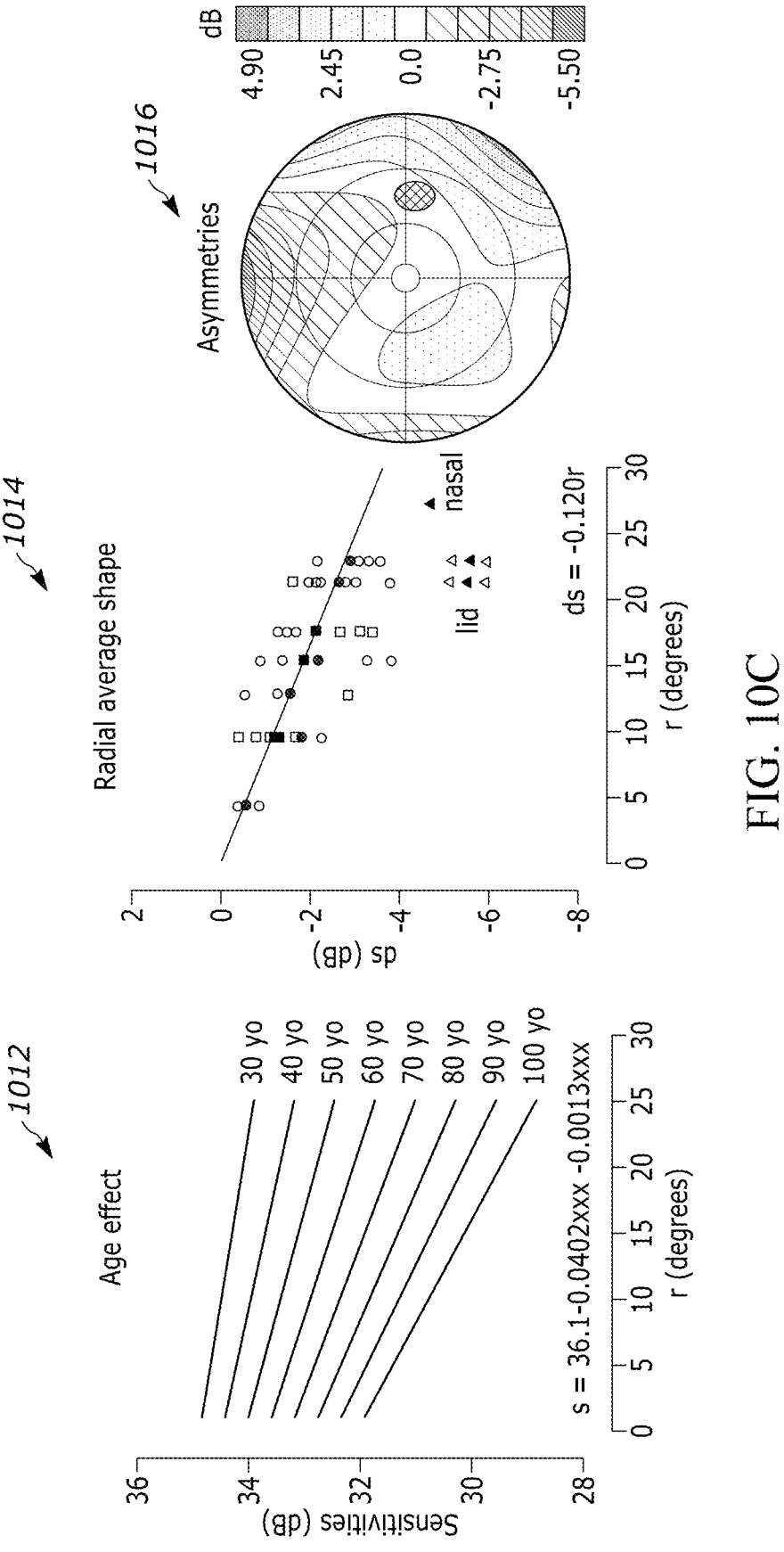
FIG. 10C illustrates an example graphs of components parts of an average hill of vision (HoV) model used in accordance with various embodiments herein.

In some embodiments, the average HoV model 1008 may include 3 different combined elements or models. In particular, these combined elements or models may include an intercept/age model 1012, an eccentricity or radial average shape model 1014, and a visual field asymmetry model 1016 as shown in FIG. 10C. In general, the intercept/age model 1012 describes a theoretical sensitivity of a 0-year-old patient at the center of vision (fovea) and documents eccentricity-dependent differences in age as a function of an subject age and distance from fovea (eccentricity). The eccentricity model generally documents linear decay of sensitivity with eccentricity and the visual field asymmetry model documents asymmetries between superior and inferior and nasal and temporal parts of a visual field using Zernike polynomials.

To find the intercept and age effect of the average HoV model 1008, a quadratic function is fit to a first set of visual field normative data (e.g., the 10-2 visual field normative data) and independently to a second set of visual field normative data (e.g., the 24-2 visual field normative data). For the second set of normal data a cross component is included to account for the known fact that the age effect increases with eccentricity. Finally, a linear component for the average (symmetric) shape of the fill of vision is added. A linear mode is used because the radial eccentricity effect is well described by a linear model. For the fit to the second set of normal data, locations corresponding to the blind spot, the 4 outermost superior locations (most affected by lid artifact), and the 2 outermost nasal locations (most affected by rim lens artifacts) were removed.

In some embodiments, the average HoV model 1008 is constructed by fitting intercept, age, eccentricity, and age-eccentricity effect followed by generating the visual field asymmetry model 1016 using Zernike coefficients for all locations (including the 4 lid and 2 outermost nasal locations) except for the two locations in the blind spot. This approach gives age and age-eccentricity coefficients of:

$$\text{Age coefficient} = -0.0402 \ dB/year$$

$$\text{Age}-\text{eccentricity coefficient} = -0.0013 \ dB/(year*degree)$$

In this age model, the age slope at the fovea is −0.04 dB/year, at locations (±10°, ±10°) slopes would all be −0.06 dB/year, and at an eccentricity of 30°, slope is −0.08 dB/year.

Figure 10D:
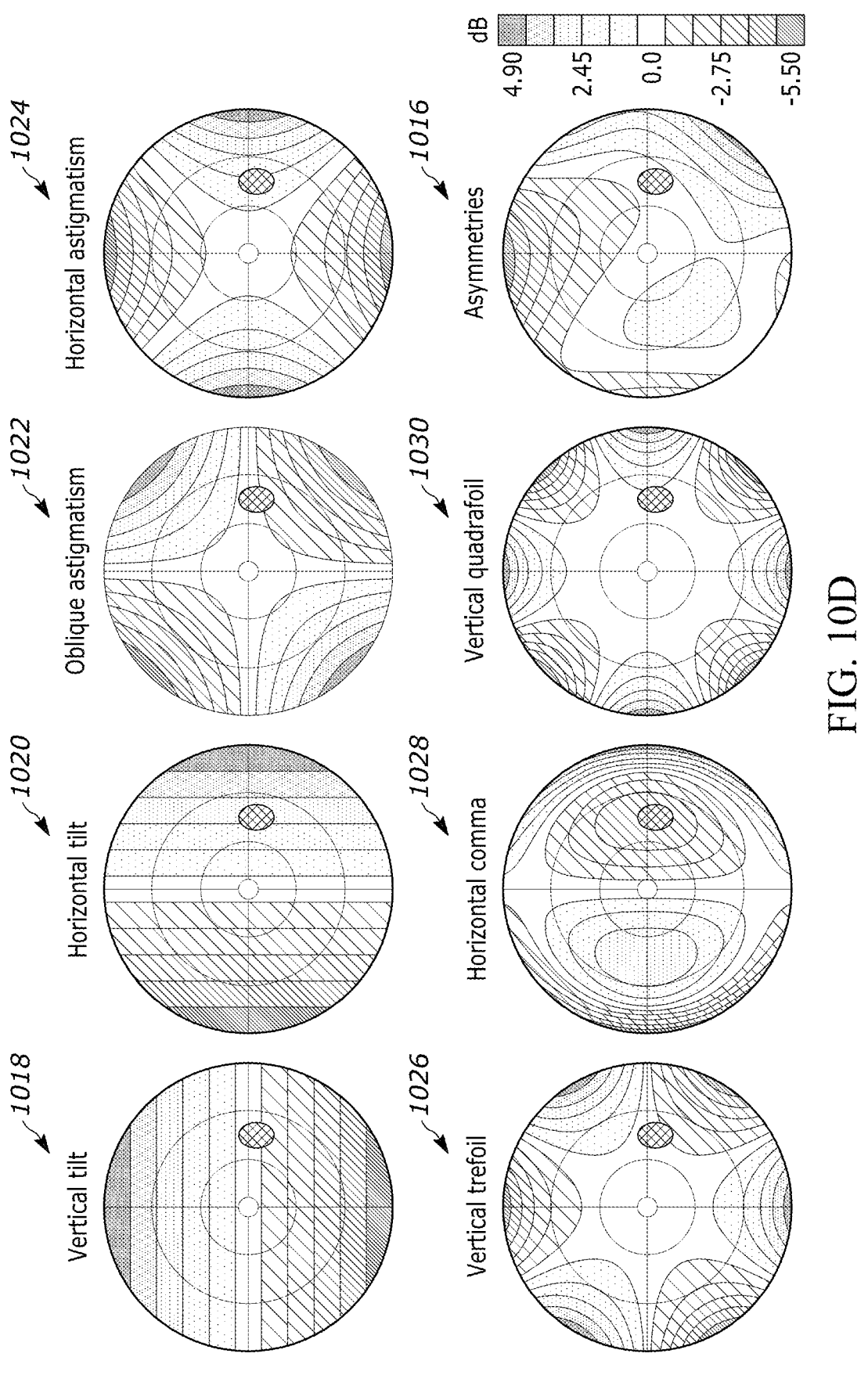
FIG. 10D illustrates example polynomials used and to describe final surface asymmetries in accordance with various embodiments herein.

FIG. 10D shows example the polynomials used and the final surface describing the asymmetries as the visual field asymmetry model 1016. In particular, the polynomials used to construct the visual field asymmetry model 1016 include representations of vertical tilt 1018, horizontal tilt 1020, oblique astigmatism 1022, horizontal astigmatism 1024, vertical trefoil 1026, horizontal comma 1028, and vertical or oblique quadrafoil 1030. The Zernike coefficients for each of these polynomials used to model the asymmetries were as follows:

$$\text{Vertical tilt: } - 0.958 \ dB/degree$$

$$\text{Horizontal tilt: } 0.517 \ dB/degree$$

$$\text{Oblique astigmatism: } - 0.221 \ dB/degree^2$$

$$\text{Horizontal astigmatism: } 0.650 \ dB/degree^2$$

$$\text{Vertical trefoil: } 0.185 \ dB/degree^3$$

$$\text{Horizontal comma: } 0.541 \ dB/degree^3$$

$$\text{Oblique quandrafoil: } - 0.452 \ dB/degree^4$$

Finally, an intercept value of 36.1 dB and Eccentricity parameter of −0.12 dB/degree are derived from the original second set of visual field normative data (e.g., 24-2 visual field normative data) by correcting for age and asymmetries and fitting a simple linear model as a function of radius from the fovea. A similar value of 36.2 dB is derived for the intercept from the first set of visual field normative data (e.g., the 10-2 visual field normative data).

With references again to FIG. 10C, it is shown that the model predicts a drop of more than 3 dB more than the radial decrease at the outermost locations north and west of the fovea. It should be appreciated that the model may be reduced to a lower number of polynomials using a different approach instead of the Zernike polynomials.

Figure 10E:
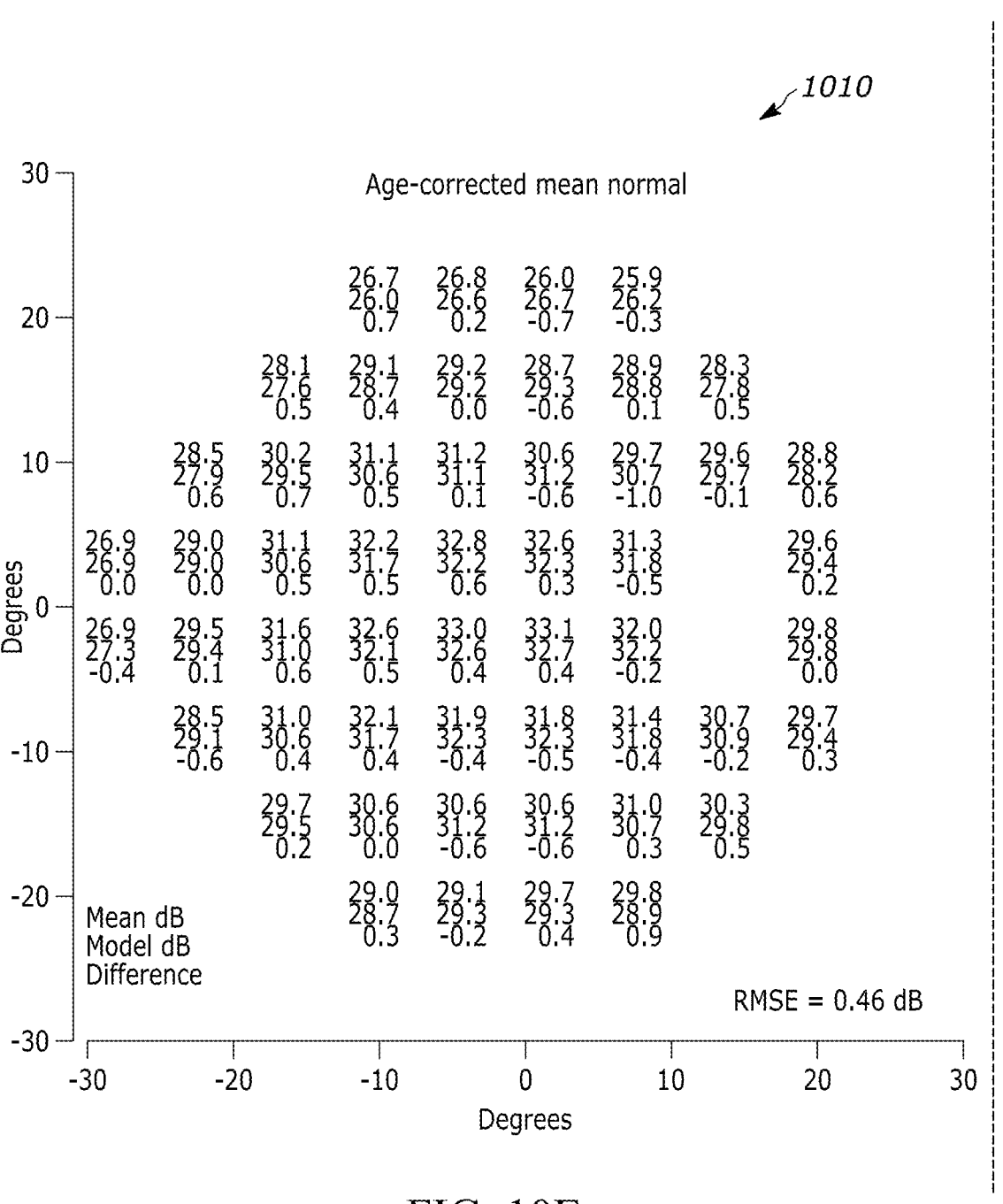
FIG. 10E illustrates an example individualized hill of vision (HoV) model, used in accordance with various embodiments herein, relative to an age corrected mean normal vision model.
Figure 10E:
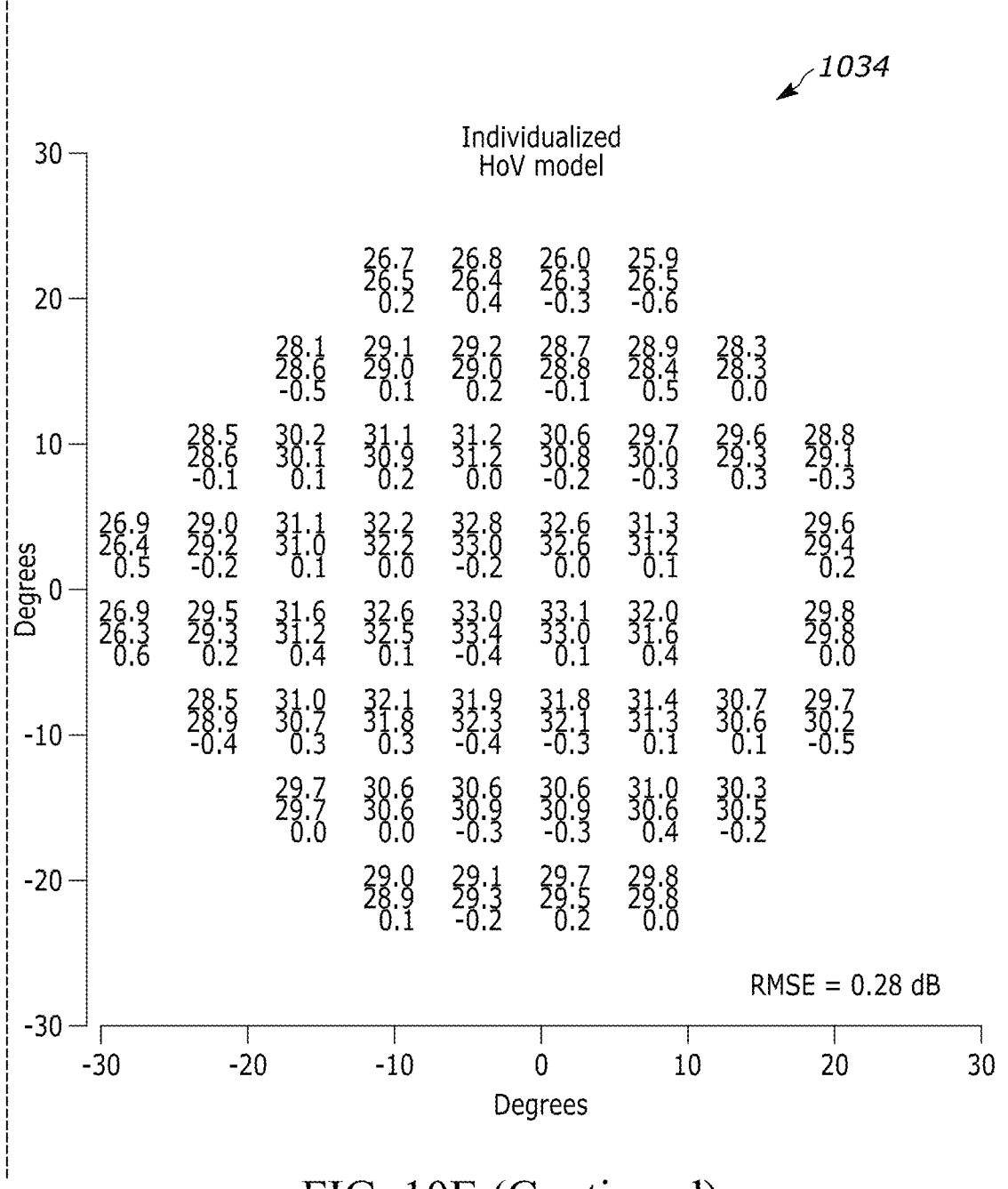

With reference now to FIG. 10E, one example of an individualized HoV model 1034 is shown in a graphical representation next to a graphical representation of the age corrected mean normal vision model 1010. As described above, the individualized HoV model 1034 is generated by the computing system 1002 (FIG. 10A) for a specific test subject wearing the headset device 1004 based on the average HoV model 1008 (FIG. 10B). As shown in FIG. 10E, the individualized HoV model 1034 by recalculating the intercept and eccentricity parameter moves the RMSE from 0.42 dB for the average HoV model 1008 to 0.28 dB for the individualized HoV model 1034.

In particular, estimation of the intercept and eccentricity effect parameters are recalculated on an individual basis for the test subject from the established average HoV model 1008 and age effect. For example, the age effect and the asymmetries are removed on all visual fields in the normative dataset. Then, for each visual field, the intercept and eccentricity parameters are obtained. In the example individualized HoV model 1034 shown in FIG. 10E, the weighted averages for the intercepts are 36.5 dB and for the eccentricity parameters are −0.159 dB/degree. This intercept is 0.4 dB greater than for the average HoV model 1008 and the average eccentricity parameter is −0.04 dB/degree lower.

When fitted to individual visual fields, both the age-corrected mean normal model 1010 and the average HoV model 1008 have an average RMSE of 2.1 dB and 2.0 dB, respectively. For the age-corrected mean normal model, the RMSE is equivalent to the RMS TD values. Similarly, the RMS of PD values is 2.5 dB. The individualized approach of the individualized HoV model 1034 shares the same goal as the conventional PD values, but instead utilizes reference deviations (RD) that account for the eccentricity effect. The RD are obtained after adjusting each visual field to the individual hill of vision height and eccentricity effect (with the strong assumption that the asymmetries are the same for all). This approach yields an average RMS RD of 1.6 dB, which represents 0.9 dB or a 36% decrease with respect to the PD values. The example individualized HoV model 1034 adjusts for age, asymmetries, and average intercept and eccentricity effect and then uses a linear model to obtain the intercept and eccentricity effect for each individual visual field. In this way, an estimate of the GH (e.g., the difference in the overall sensitivity from mean normal to the individual field) as the intercept of the fit.

An estimate of eccentricity effect noted by a model is defined as the slope of the fit (e.g., the difference in steepness of the hill of vision from mean normal to the individual field). Furthermore, the advantages of the individualized HoV model 1034 over alternative approaches may be assessed by estimating the interindividual differences in GH and eccentricity effect may and comparing the estimates against conventional models by subtracting the 7th most sensitive TD value of the field. The example individualized HoV 1034 includes a central 95% distribution of GH that falls within ±2.3 dB and a central 95% distribution of eccentricity effects that falls within ±0.11 dB/degree, which means that differences at 30° range from and to ±3.3 dB due only to eccentricity effects. When compared against the conventional estimation (using the 7th most sensitive TD value), the mean difference is 1.8 dB the difference between the GH estimate and GH7 changes considerably as a function of the estimated eccentricity effect, where shallower visual fields yield smaller GH7 estimates and steeper visual fields yield greater GH7 estimates compared to the GH estimates of the example individualized HoV 1034.

ASPECTS OF THE DISCLOSURE

The following aspects are provided as examples in accordance with the disclosure herein and are not intended to limit the scope of the disclosure. Furthermore, Aspects 1-9 regard systems and methods for glaucoma diagnosis and monitoring by implementing adaptive map perimetry; Aspects 10-30 regard systems and methods systems and methods for automatically assessing visual field testing; Aspects 31-44 regard systems and methods for glaucoma diagnosis and monitoring by implementing adaptive map perimetry; and Aspects 45-64 regard visual field analysis systems and methods for automatically assessing visual field testing.

Aspect 1. A visual field (VF) analysis system configured for glaucoma diagnosis and monitoring by implementing adaptive map perimetry, the VF analysis system comprising: a headset device (e.g., a virtual reality (VR) device) comprising a display screen positioned proximate to, or within a viewable distance from, a user's eyes, the headset device communicatively coupled to one or more processors; and an adaptive map perimetry algorithm comprising computing instructions stored on a memory accessible by one or more processors, a normative database or model, wherein the adaptive map perimetry algorithm is configured to access or implement the normative database or model to adapt the headset device to be device-agnostic with respect to one or more differently configured headset devices; wherein the computing instructions of the adaptive map perimetry algorithm, when executed by the one or more processors, are configured to cause the one or more processors to implement a VF test comprising: implement a VF test on the display screen of the headset device, wherein the VF test is adapted to fit an area of the display screen based on values in the normative database or model, wherein the VF test is rendered as a same or similar visualization compared to one or more different headset devices having different display screens having different respective shapes, formats, sizes, and/or resolutions; receive visual test data indicating a visual field of the user, detect, based on the visual test data, one or more initial test locations specific to the user, the one or more initial test locations defining one or more healthy clusters indicative of an absence of scatoma and one or more damaged clusters indicative of scotoma, and generate, based on the one or more initial test locations, a spatial mapping identifying locations of the one or more damaged clusters.

Aspect 2. The VF analysis system of aspect 1, wherein the locations of the spatial mapping are separated by a 0.5 degree or 0.5 resolution from a vertical angle and/or horizontal angle.

Aspect 3. The VF analysis system of aspects 1 or 2, wherein the normative database or model comprises normative values generated from quantile regression, wherein the quantile regression comprises generating the normative values from normative reference values comprising biometric measurements, such as refraction, axial length, corneal curvature, or other independent variables comprising biometric measurements of the user's eyes, wherein the headset device is updated with or has access to the normative database or model to calibrate the headset device as device-agnostic when implementing the adaptive map perimetry algorithm.

Aspect 4. A visual field (VF) analysis method for glaucoma diagnosis and monitoring by implementing adaptive map perimetry, the VF analysis method comprising: implementing a VF test on a display screen of an electronic display screen device (e.g., a virtual reality (VR) device), wherein the electronic display screen device comprises a display screen positioned proximate to, or within a viewable distance from, a user's eyes, the electronic display screen device communicatively coupled to one or more processors, and wherein the VF test is adapted to fit an area of the display screen based on values in a normative database or model, wherein the VF test is rendered as a same or similar visualization compared to one or more different electronic display screen devices having different display screens having different respective shapes, formats, sizes, and/or resolutions, wherein an adaptive map perimetry algorithm is configured to access or implement the normative database or model to adapt the electronic display screen device to be device-agnostic with respect to the one or more differently configured electronic display screen devices, receiving visual test data indicating a visual field of the user; detecting, based on the visual test data, one or more initial test locations specific to the user, the one or more initial test locations defining one or more healthy clusters indicative of an absence of scatoma and one or more damaged clusters indicative of scotoma; and generating, based on the one or more initial test locations, a spatial mapping identifying locations of the one or more damaged clusters.

Aspect 5. The VF analysis method of aspect 4, wherein the locations of the spatial mapping are separated by a 0.5 degree or 0.5 resolution from a vertical angle and/or horizontal angle.

Aspect 6. The VF analysis method of aspect 4 or 5, wherein the normative database or model comprises normative values generated from quantile regression, wherein the quantile regression comprises generating the normative values from normative reference values comprising biometric measurements, such as refraction, axial length, corneal curvature, or other independent variables comprising biometric measurements of the user's eyes, wherein the electronic display screen device is updated with or has access to the normative database or model to calibrate the electronic display screen device as device-agnostic when implementing the adaptive map perimetry algorithm.

Aspect 7. A tangible, non-transitory computer-readable medium storing instructions for glaucoma diagnosis and monitoring by implementing adaptive map perimetry, that when executed by one or more processors cause the one or more processors to: implement a VF test on a display screen of an electronic display screen device (e.g., a virtual reality (VR) device), wherein the electronic display screen device comprises a display screen positioned proximate to, or within a viewable distance from, a user's eyes, the electronic display screen device communicatively coupled to the one or more processors, and wherein the VF test is adapted to fit an area of the display screen based on values in a normative database or model, wherein the VF test is rendered as a same or similar visualization compared to one or more different electronic display screen devices having different display screens having different respective shapes, formats, sizes, and/or resolutions, wherein an adaptive map perimetry algorithm is configured to access or implement the normative database or model to adapt the electronic display screen device to be device-agnostic with respect to the one or more differently configured electronic display screen devices, receive visual test data indicating a visual field of the user; detect, based on the visual test data, one or more initial test locations specific to the user, the one or more initial test locations defining one or more healthy clusters indicative of an absence of scatoma and one or more damaged clusters indicative of scotoma; and generate, based on the one or more initial test locations, a spatial mapping identifying locations of the one or more damaged clusters.

Aspect 8. The tangible, non-transitory computer-readable medium of aspect 7, wherein the locations of the spatial mapping are separated by a 0.5 degree or 0.5 resolution from a vertical angle and/or horizontal angle.

Aspect 9. The tangible, non-transitory computer-readable medium of aspect 7 or 8, wherein the normative database or model comprises normative values generated from quantile regression, wherein the quantile regression comprises generating the normative values from normative reference values comprising biometric measurements, such as refraction, axial length, corneal curvature, or other independent variables comprising biometric measurements of the user's eyes, wherein the electronic display screen device is updated with or has access to the normative database or model to calibrate the electronic display screen device as device-agnostic when implementing the adaptive map perimetry algorithm.

Aspect 10. A visual field feedback (VFF) system configured for automatically assessing visual field testing, the VFF system comprising: a headset device (e.g., a virtual reality (VR) device) comprising a display screen positioned proximate to, or within a viewable distance from a user's eyes, the headset device communicatively coupled to one or more processors; and computing instructions stored on a computer memory and, when executed by one or more processors, cause the one or more processors to: display a stimulus to a test subject (e.g., a patient), store in computer memory a response of the test subject to the displayed stimulus, analyze the response based on a location of the displayed stimulus, provide feedback to the test subject based on the response and analysis.

Aspect 11. The VFF system of aspect 10, wherein the test subject response can include recognizing and acknowledging the stimulus via interaction with a controller or not recognizing or acknowledging the stimulus by not interacting with the controller.

Aspect 12. The VFF system of aspect 10 or 11, wherein the test subject response can include (a) whether the test subject (e.g., patient) response is a hit or miss; (b) a response time of the test subject (e.g. patient); (c) a location of the stimulus; (d) a gaze position of the test subject (e.g. patient); (e) eye movement of the test subject; and/or (f) a Time-of-Response (e.g., time of response of the VFF system).

Aspect 13. The VFF system of any of aspects 10-12, wherein the feedback can include any of visual, audio, tactile, or haptic feedback.

Aspect 14. The VFF system of any of aspects 10-13, wherein the feedback is correlated to accuracy of the responses of the test subject.

Aspect 15. The VFF system of any of aspects 10-14, wherein the feedback can be positive or negative.

Aspect 16. The VFF system of any of aspects 10-15, wherein positive feedback is displayed if the test subject responds correctly and negative feedback is displayed if the test subject responds incorrectly.

Aspect 17. The VFF system of any of aspects 10-16, wherein the system is used for any of visual field testing, rehabilitation from disease or injury, diagnostic and/or therapeutic purposes, visual performance enhancement, or visual function training.

Aspect 18. The VFF system of any of aspects 10-17, wherein the feedback is formatted into a format that can be stored on a server and provided a test subject on a computer network.

Aspect 19. The VFF system of any of aspects 10-18, wherein the analyzing the response based on the location of the displayed stimulus comprises: inputting, into an AI model executing on the more or more processors, the response, wherein the AI model is trained with training data comprising response feedback of test subjects (e.g., button presses, eye-motion, or other such feedback provided by the user), wherein the AI model is configured to output a prediction defining an accuracy value corresponding to a percentage that a test subject correctly responded to the displayed stimulus; generating, by the AI model and based on the prediction defining the accuracy value, the feedback to the test subject.

Aspect 20. A visual field feedback (VFF) method for automatically assessing visual field testing, the method comprising: displaying, on a headset device (e.g., a virtual reality (VR) device), a stimulus to a test subject (e.g., patient); recording, by one or more processors, a test subject's response to the displayed stimulus; analyzing, by a Visual Field Feedback system, a test subject's response to the displayed stimulus using a stimulus location; providing feedback to the test subject based on the response and analysis.

Aspect 21. The VFF method of aspect 20, wherein the test subject's response can include recognizing and acknowledging the stimulus via interaction with a controller or not recognizing or acknowledging the stimulus by not interacting with the controller.

Aspect 22. The VFF method of aspect 20 or 21, wherein the test subject's response can include (a) whether the test subject (e.g., patient) response is a hit or miss; (b) a response time of the test subject (e.g. patient); (c) a location of the stimulus; (d) a gaze position of the test subject (e.g. patient); (e) an eye movement of the test subject; (f) a Time-of-Response (e.g., time of response of the VFF system).

Aspect 23. The VFF method of any of aspects 20-22, wherein the feedback can include any of visual, audio, tactile, or haptic feedback.

Aspect 24. The VFF method of any of aspects 20-23, wherein the feedback is correlated to accuracy of the responses of the test subject.

Aspect 25. The VFF method of any of aspects 20-24, wherein the feedback can be positive or negative.

Aspect 26. The VFF method of any of aspects 20-25, wherein positive feedback is displayed if the test subject responds correctly and negative feedback is displayed if the test subject responds incorrectly.

Aspect 27. The VFF method of any of aspects 20-26, wherein the method is used for any of visual field testing, rehabilitation from disease or injury, diagnostic and/or therapeutic purposes, visual performance enhancement, or visual function training.

Aspect 28. The VFF method of any of aspects 20-27, wherein the feedback is formatted into a format that can be stored on a server and provided a test subject over a computer network.

Aspect 29. The VFF method of any of aspects 20-28, wherein the analyzing the response based on the location of the displayed stimulus comprises: inputting, into an AI model executing on the more or more processors, the response, wherein the AI model is trained with training data comprising response feedback of test subjects (e.g., button presses, eye-motion, or other such feedback provided by the user), wherein the AI model is configured to output a prediction defining an accuracy value corresponding to a percentage that a test subject correctly responded to the displayed stimulus; generating, by the AI model and based on the prediction defining the accuracy value, the feedback to the test subject.

Aspect 30. A tangible, non-transitory computer-readable medium storing instructions for automatically assessing visual field testing, that when executed by one or more processors cause the one or more processors to: display, on a headset device (e.g., a virtual reality (VR) device), a stimulus to a test subject (e.g., patient); record, by one or more processors, a test subject's response to the displayed stimulus; analyze, by a Visual Field Feedback system, a test subject's response to the displayed stimulus using a stimulus location; provide feedback to the test subject based on the response and analysis.

Aspect 31. A visual field (VF) analysis system configured for glaucoma diagnosis and monitoring by implementing adaptive map perimetry, the VF analysis system comprising: a headset device (e.g., a virtual reality (VR) device) comprising a display screen positioned proximate to, or within a viewable distance from, a user's eyes, the headset device communicatively coupled to one or more processors; and an adaptive map perimetry algorithm comprising computing instructions stored on a memory accessible by one or more processors, a normative database or model, wherein the adaptive map perimetry algorithm is configured to access or implement the normative database or model to adapt the headset device to be device-agnostic with respect to one or more differently configured headset devices; wherein the computing instructions of the adaptive map perimetry algorithm, when executed by the one or more processors, are configured to cause the one or more processors to implement a VF test comprising: implement a VF test on the display screen of the headset device, wherein the VF test is adapted to fit an area of the display screen based on values in the normative database or model, wherein the VF test is rendered as a same or similar visualization compared to one or more different headset devices having different display screens having different respective shapes, formats, sizes, and/or resolutions; receive visual test data indicating a visual field of the user, detect, based on the visual test data, one or more initial test locations specific to the user, the one or more initial test locations defining one or more healthy clusters indicative of an absence of scatoma and one or more damaged clusters indicative of scotoma, generate, based on the one or more initial test locations, a spatial mapping identifying locations of the one or more damaged clusters, display a stimulus to a test subject (e.g., a patient), store in computer memory a response of the test subject to the displayed stimulus, analyze the response based on a location of the displayed stimulus and/or the spatial mapping, provide feedback to the test subject based on the response and analysis.

Aspect 32. The VF analysis system of aspect 31, wherein the locations of the spatial mapping are separated by a 0.5 degree or 0.5 resolution from a vertical angle and/or horizontal angle.

Aspect 33. The VF analysis system of aspect 31 or 32, wherein the normative database or model comprises normative values generated from quantile regression, wherein the quantile regression comprises generating the normative values from normative reference values comprising biometric measurements, such as refraction, axial length, corneal curvature, or other independent variables comprising biometric measurements of the user's eyes, wherein the headset device is updated with or has access to the normative database or model to calibrate the headset device as device-agnostic when implementing the adaptive map perimetry algorithm.

Aspect 34. The VF analysis system of any of aspects 31-33, wherein the test subject response can include recognizing and acknowledging the stimulus via interaction with a controller or not recognizing or acknowledging the stimulus by not interacting with the controller.

Aspect 35. The VF analysis system of any of aspects 31-34, wherein the test subject response can include (a) whether the test subject (e.g., patient) response is a hit or miss; (b) a response time of the test subject (e.g. patient); (c)

a location of the stimulus; (d) a gaze position of the test subject (e.g. patient); (e) eye movement of the test subject; and/or (f) a Time-of-Response (e.g., time of response of the VFF system).

Aspect 36. The VF analysis system of any of aspects 31-35, wherein the feedback can include any of visual, audio, tactile, or haptic feedback.

Aspect 37. The VF analysis system of any of aspects 31-36, wherein the feedback is correlated to accuracy of the responses of the test subject.

Aspect 38. The VF analysis system of any of aspects 31-37, wherein the feedback can be positive or negative.

Aspect 39. The VF analysis system of any of aspects 31-38, wherein positive feedback is displayed if the test subject responds correctly and negative feedback is displayed if the test subject responds incorrectly.

Aspect 40. The VF analysis system of any of aspects 31-39, wherein the system is used for any of visual field testing, rehabilitation from disease or injury, diagnostic and/or therapeutic purposes, visual performance enhancement, or visual function training.

Aspect 41. The VF analysis system of any of aspects 31-40, wherein the feedback is formatted into a format that can be stored on a server and provided a test subject on a computer network.

Aspect 42. The VF analysis system of any of aspects 31-41, wherein the analyzing the response based on the location of the displayed stimulus comprises: inputting, into an AI model executing on the more or more processors, the response, wherein the AI model is trained with training data comprising response feedback of a plurality of test subjects (e.g., button presses, eye-motion, or other such feedback provided by the user) and/or spatial mapping of a plurality of test subjects, wherein the AI model is configured to output a prediction defining an accuracy value corresponding to a percentage that a test subject correctly responded to the displayed stimulus based on the test subject's spatial mapping; generating, by the AI model and based on the prediction defining the accuracy value, the feedback to the test subject.

Aspect 43. A visual field (VF) analysis method for glaucoma diagnosis and monitoring by implementing adaptive map perimetry, the VF analysis method comprising: implementing a VF test on a display screen of an electronic display screen device (e.g., a virtual reality (VR) device), wherein the electronic display screen device comprises a display screen positioned proximate to, or within a viewable distance from, a user's eyes, the electronic display screen device communicatively coupled to one or more processors, and wherein the VF test is adapted to fit an area of the display screen based on values in a normative database or model, wherein the VF test is rendered as a same or similar visualization compared to one or more different electronic display screen devices having different display screens having different respective shapes, formats, sizes, and/or resolutions, wherein an adaptive map perimetry algorithm is configured to access or implement the normative database or model to adapt the electronic display screen device to be device-agnostic with respect to the one or more differently configured electronic display screen devices, receiving visual test data indicating a visual field of the user; detecting, based on the visual test data, one or more initial test locations specific to the user, the one or more initial test locations defining one or more healthy clusters indicative of an absence of scatoma and one or more damaged clusters indicative of scotoma; generating, based on the one or more initial test locations, a spatial mapping identifying locations of the one or more damaged clusters; displaying, on a headset device (e.g., a virtual reality (VR) device), a stimulus to a test subject (e.g., patient); recording, by one or more processors, a test subject's response to the displayed stimulus; analyzing, by a Visual Field Feedback system (e.g., the VR device), a test subject's response to the displayed stimulus using a stimulus location and/or the spatial mapping; providing feedback to the test subject based on the response and analysis.

Aspect 44. A tangible, non-transitory computer-readable medium storing instructions for glaucoma diagnosis and monitoring by implementing adaptive map perimetry, that when executed by one or more processors cause the one or more processors to: implement a VF test on a display screen of an electronic display screen device (e.g., a virtual reality (VR) device), wherein the electronic display screen device comprises a display screen positioned proximate to, or within a viewable distance from, a user's eyes, the electronic display screen device communicatively coupled to the one or more processors, and wherein the VF test is adapted to fit an area of the display screen based on values in a normative database or model, wherein the VF test is rendered as a same or similar visualization compared to one or more different electronic display screen devices having different display screens having different respective shapes, formats, sizes, and/or resolutions, wherein an adaptive map perimetry algorithm is configured to access or implement the normative database or model to adapt the electronic display screen device to be device-agnostic with respect to the one or more differently configured electronic display screen devices, receive visual test data indicating a visual field of the user; detect, based on the visual test data, one or more initial test locations specific to the user, the one or more initial test locations defining one or more healthy clusters indicative of an absence of scatoma and one or more damaged clusters indicative of scotoma; generate, based on the one or more initial test locations, a spatial mapping identifying locations of the one or more damaged clusters; display, on a headset device (e.g., a virtual reality (VR) device), a stimulus to a test subject (e.g., patient); record, by one or more processors, a test subject's response to the displayed stimulus; analyze, by a Visual Field Feedback system (e.g., the VR device), a test subject's response to the displayed stimulus using a stimulus location and/or the spatial mapping; provide feedback to the test subject based on the response and analysis.

Aspect 45. A visual field analysis (VFA) system configured for automatically assessing visual field testing, the VFA system comprising: a headset device (e.g., a virtual reality (VR) device) comprising a display screen positioned proximate to, or within a viewable distance from a user's eyes, the headset device communicatively coupled to one or more processors; an average hill of vision model (HoV) saved in a computer memory; and computing instructions stored on the computer memory and, when executed by one or more processors, cause the one or more processors to: generate an eye difference estimate for a test subject relative to reference data for an average healthy eye obtained from a normative dataset, the eye difference estimate indicating a difference in (1) overall sensitivity or general height (GH) and (2) the rate of sensitivity decay with eccentricity (distance from the fovea) relative to the reference data; generate an individualized HoV model based on the eye difference estimate and the average HoV model; display, on the headset device, a respective stimulus to the test subject at a plurality of test locations; store in computer memory responses of the test subject to the respective stimulus displayed at the plurality of test locations; analyze the responses to determine a respective sensitivity value for the test subject at each of the plurality of test locations; determine total-deviation values for the test subject by subtracting the respective sensitivity value for each of the plurality of test locations from a corresponding value of the individualized HoV model; analyze the total-deviation values; and provide feedback to the test subject based on the analysis.

Aspect 46. The VFA system of aspect 45 wherein to generate the eye difference estimate the computing instructions, when executed by one or more processors, cause the one or more processors to: determine a set of preliminary test locations; display, on the headset device, a visual psychophysics algorithm at the set of preliminary test locations to obtain preliminary sensitivities; and determine the overall sensitivity or GH and the rate of sensitivity decay with eccentricity of the eye difference estimate based on the preliminary sensitivities.

Aspect 47. The VFA system of aspect 45 or 46 wherein to generate the eye difference estimate the computing instructions, when executed by one or more processors, cause the one or more processors to: generate initial estimates of the overall sensitivity or GH and the rate of sensitivity decay with eccentricity; obtain interim responses of the test subject to the respective stimulus displayed at the plurality of test locations analyze the interim responses to adjust the initial estimates of the overall sensitivity or GH and the rate of sensitivity decay with eccentricity and obtain confidence intervals; adjust levels of the respective stimulus displayed on the headset device based on the adjusted initial estimates to obtain respective sensitivity value for the test subject at each of the plurality of test locations; and determine the overall sensitivity or GH and the rate of sensitivity decay with eccentricity of the eye difference estimate based on the respective sensitivity value for the test subject at each of the plurality of test locations.

Aspect 48. The VFA system of any of aspects 45-47 wherein the initial estimates include one or more of age-corrected mean normal values, values generated from analysis of one or more previous visual field tests, or values from a preliminary test administered to the test subject.

Aspect 49. The VFA system of any of aspects 45-48 wherein the responses of the test subject to the respective stimulus displayed at the plurality of test locations comprise a visual field and to generate the eye difference estimate the computing instructions, when executed by one or more processors, cause the one or more processors to: identify points in the visual field that are damaged; remove the damaged points from the visual field; analyze the remaining points within the visual field to generate the eye difference estimate and fit the individualized HoV model.

Aspect 50. The VFA system of any of aspects 45-49 wherein one of a least-squares algorithm, maximum-likelihood algorithm, Bayesian algorithm, or Machine Learning algorithm are used to generate the eye difference estimate and fit the individualized HoV model.

Aspect 51. The VFA system of any of aspects 45-50 wherein the average HoV model includes a combination of an intercept/age model, an eccentricity model, and a visual field asymmetry model.

Aspect 52. The VFA system of any of aspects 45-51 wherein the intercept model describes a theoretical sensitivity of a 0-year-old patient at the center of vision (fovea).

Aspect 53. The VFA system of any of aspects 45-52 wherein the age model documents eccentricity-dependent differences in age as a function of an subject age and distance from fovea (eccentricity).

Aspect 54. The VFA system of any of aspects 45-53 wherein the eccentricity model documents linear decay of sensitivity with eccentricity.

Aspect 55. The VFA system of any of aspects 45-54 wherein the visual field asymmetry model documents asymmetries between superior and inferior and nasal and temporal parts of a visual field using Zernike polynomials.

Aspect 56. A visual field analysis (VFA) method for automatically assessing visual field testing, the VFA method comprising: generating an eye difference estimate for a test subject relative to reference data for an average healthy eye obtained from a normative dataset, the eye difference estimate indicating a difference in (1) overall sensitivity or general height (GH) and (2) the rate of sensitivity decay with eccentricity (distance from the fovea) relative to the reference data; generating an individualized HoV model based on the eye difference estimate and an average HoV model saved in a computer memory; displaying, on a headset device, a respective stimulus to the test subject at a plurality of test locations, wherein the headset device (e.g., a virtual reality (VR) device) comprises a display screen positioned proximate to, or within a viewable distance from a user's eyes; storing in computer memory responses of the test subject to the respective stimulus displayed at the plurality of test locations; analyzing the responses to determine a respective sensitivity value for the test subject at each of the plurality of test locations; determining total-deviation values for the test subject by subtracting the respective sensitivity value for each of the plurality of test locations from a corresponding value of the individualized HoV model; analyzing the total-deviation values; and providing feedback to the test subject based on the analysis.

Aspect 57. The VFA method of aspect 56 wherein to generating the eye difference estimate includes: determining a set of preliminary test locations; displaying, on the headset device, a visual psychophysics algorithm at the set of preliminary test location to obtain preliminary sensitivities; and determining the overall sensitivity or GH and the rate of sensitivity decay with eccentricity of the eye difference estimate based on the preliminary sensitivities.

Aspect 58. The VFA method of aspects 56 or 57 wherein to generating the eye difference estimate includes: generating initial estimates of the overall sensitivity or GH and the rate of sensitivity decay with eccentricity; obtaining interim responses of the test subject to the respective stimulus displayed at the plurality of test locations analyzing the interim responses to adjust the initial estimates of the overall sensitivity or GH and the rate of sensitivity decay with eccentricity and obtain confidence intervals; adjusting levels of the respective stimulus displayed on the headset device based on the adjusted initial estimates to obtain respective sensitivity value for the test subject at each of the plurality of test locations; and determining the overall sensitivity or GH and the rate of sensitivity decay with eccentricity of the eye difference estimate based on the respective sensitivity value for the test subject at each of the plurality of test locations.

Aspect 59. The VFA method of any of aspects 56-58 wherein the initial estimates include one or more of age-corrected mean normal values, values generated from analysis of one or more previous visual field tests, or values from a preliminary test administered to the test subject.

Aspect 60. The VFA method of any of aspects 56-59 wherein the responses of the test subject to generating the eye difference estimate includes: identifying points in the visual field that are damaged; removing the damaged points from the visual field; analyzing the remaining points within the visual field to generate the eye difference estimate and fit the individualized HoV model.

Aspect 61. The VFA method of any of aspects 56-60 wherein one of a least-squares algorithm, maximum-likelihood algorithm, Bayesian algorithm, or Machine Learning algorithm are used to generate the eye difference estimate and fit the individualized HoV model.

Aspect 62. The VFA method of any of aspects 56-61 wherein the average HoV model includes a combination of an intercept/age model, an eccentricity model, and a visual field asymmetry model.

Aspect 63. A tangible, non-transitory computer-readable medium storing instructions for automatically assessing visual field testing, that when executed by one or more processors cause the one or more processors to: generate an eye difference estimate for a test subject relative to reference data for an average healthy eye obtained from a normative dataset, the eye difference estimate indicating a difference in (1) overall sensitivity or general height (GH) and (2) the rate of sensitivity decay with eccentricity (distance from the fovea) relative to the reference data; generate an individualized HoV model based on the eye difference estimate and an average HoV model saved in a computer memory; display, on a headset device, a respective stimulus to the test subject at a plurality of test locations, wherein the headset device (e.g., a virtual reality (VR) device) comprises a display screen positioned proximate to, or within a viewable distance from a user's eyes; store in computer memory responses of the test subject to the respective stimulus displayed at the plurality of test locations; analyze the responses to determine a respective sensitivity value for the test subject at each of the plurality of test locations; determine total-deviation values for the test subject by subtracting the respective sensitivity value for each of the plurality of test locations from a corresponding value of the individualized HoV model; analyze the total-deviation values; and provide feedback to the test subject based on the analysis.

Aspect 64. The tangible, non-transitory computer-readable medium of aspect 63 wherein the average HoV model includes a combination of an intercept/age model, an eccentricity model, and a visual field asymmetry model.

ADDITIONAL CONSIDERATIONS

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. One may be implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A visual field analysis (VFA) system configured for automatically assessing visual field testing, the VFA system comprising:

a headset device comprising a display screen positioned proximate to, or within a viewable distance from a user's eyes, the headset device communicatively coupled to one or more processors;

an average hill of vision model (HoV) saved in a computer memory; and computing instructions stored on the computer memory and, when executed by one or more processors, cause the one or more processors to:

generate an eye difference estimate for a test subject relative to reference data for an average healthy eye obtained from a normative dataset, the eye difference estimate indicating a difference in (1) overall sensitivity or general height (GH) and (2) the rate of sensitivity decay with eccentricity (distance from the fovea) relative to the reference data;

generate an individualized HoV model based on the eye difference estimate and the average HoV model;

display, on the headset device, a respective stimulus to the test subject at a plurality of test locations;

store in computer memory responses of the test subject to the respective stimulus displayed at the plurality of test locations;

analyze the responses to determine a respective sensitivity value for the test subject at each of the plurality of test locations;

determine total-deviation values for the test subject by subtracting the respective sensitivity value for each of the plurality of test locations from a corresponding value of the individualized HoV model;

analyze the total-deviation values; and provide feedback to the test subject based on the analysis.

2. The VFA system of claim 1 wherein to generate the eye difference estimate the computing instructions, when executed by one or more processors, cause the one or more processors to:

determine a set of preliminary test locations;

display, on the headset device, a visual psychophysics algorithm at the set of preliminary test location to obtain preliminary sensitivities; and determine the overall sensitivity or GH and the rate of sensitivity decay with eccentricity of the eye difference estimate based on the preliminary sensitivities.

3. The VFA system of claim 1 wherein to generate the eye difference estimate the computing instructions, when executed by one or more processors, cause the one or more processors to:

generate initial estimates of the overall sensitivity or GH and the rate of sensitivity decay with eccentricity;

obtain interim responses of the test subject to the respective stimulus displayed at the plurality of test locations analyze the interim responses to adjust the initial estimates of the overall sensitivity or GH and the rate of sensitivity decay with eccentricity and obtain confidence intervals;

adjust levels of the respective stimulus displayed on the headset device based on the adjusted initial estimates to obtain respective sensitivity value for the test subject at each of the plurality of test locations; and determine the overall sensitivity or GH and the rate of sensitivity decay with eccentricity of the eye difference estimate based on the respective sensitivity value for the test subject at each of the plurality of test locations.

4. The VFA system of claim 3 wherein the initial estimates include one or more of age-corrected mean normal values, values generated from analysis of one or more previous visual field tests, or values from a preliminary test administered to the test subject.

5. The VFA system of claim 1 wherein the responses of the test subject to the respective stimulus displayed at the plurality of test locations comprise a visual field and to generate the eye difference estimate the computing instructions, when executed by one or more processors, cause the one or more processors to:

identify points in the visual field that are damaged;
remove the damaged points from the visual field;
analyze the remaining points within the visual field to generate the eye difference estimate and fit the individualized HoV model.

6. The VFA system of claim 5 wherein one of a least-squares algorithm, maximum-likelihood algorithm, Bayesian algorithm, or Machine Learning algorithm are used to generate the eye difference estimate and fit the individualized HoV model.

7. The VFA system of claim 1 wherein the average HoV model includes a combination of an intercept/age model, an eccentricity model, and a visual field asymmetry model.

8. The VFA system of claim 7 wherein the intercept model describes a theoretical sensitivity of a 0-year-old patient at the center of vision (fovea).

9. The VFA system of claim 7 wherein the age model documents eccentricity-dependent differences in age as a function of an subject age and distance from fovea (eccentricity).

10. The VFA system of claim 7 wherein the eccentricity model documents linear decay of sensitivity with eccentricity.

11. The VFA system of claim 7 wherein the visual field asymmetry model documents asymmetries between superior and inferior and nasal and temporal parts of a visual field using Zernike polynomials.

12. A visual field analysis (VFA) method for automatically assessing visual field testing, the VFA method comprising:

generating an eye difference estimate for a test subject relative to reference data for an average healthy eye obtained from a normative dataset, the eye difference estimate indicating a difference in (1) overall sensitivity or general height (GH) and (2) the rate of sensitivity decay with eccentricity (distance from the fovea) relative to the reference data;
generating an individualized HoV model based on the eye difference estimate and an average HoV model saved in a computer memory;
displaying, on a headset device, a respective stimulus to the test subject at a plurality of test locations, wherein the headset device comprises a display screen positioned proximate to, or within a viewable distance from a user's eyes;
storing in computer memory responses of the test subject to the respective stimulus displayed at the plurality of test locations;
analyzing the responses to determine a respective sensitivity value for the test subject at each of the plurality of test locations;
determining total-deviation values for the test subject by subtracting the respective sensitivity value for each of the plurality of test locations from a corresponding value of the individualized HoV model;
analyzing the total-deviation values; and
providing feedback to the test subject based on the analysis.

13. The VFA method of claim 12 wherein to generating the eye difference estimate includes:

determining a set of preliminary test locations;
displaying, on the headset device, a visual psychophysics algorithm at the set of preliminary test location to obtain preliminary sensitivities; and
determining the overall sensitivity or GH and the rate of sensitivity decay with eccentricity of the eye difference estimate based on the preliminary sensitivities.

14. The VFA method of claim 12 wherein to generating the eye difference estimate includes:

generating initial estimates of the overall sensitivity or GH and the rate of sensitivity decay with eccentricity;
obtaining interim responses of the test subject to the respective stimulus displayed at the plurality of test locations
analyzing the interim responses to adjust the initial estimates of the overall sensitivity or GH and the rate of sensitivity decay with eccentricity and obtain confidence intervals;
adjusting levels of the respective stimulus displayed on the headset device based on the adjusted initial estimates to obtain respective sensitivity value for the test subject at each of the plurality of test locations; and
determining the overall sensitivity or GH and the rate of sensitivity decay with eccentricity of the eye difference estimate based on the respective sensitivity value for the test subject at each of the plurality of test locations.

15. The VFA method of claim 14 wherein the initial estimates include one or more of age-corrected mean normal values, values generated from analysis of one or more previous visual field tests, or values from a preliminary test administered to the test subject.

16. The VFA method of claim 12 wherein the responses of the test subject to generating the eye difference estimate includes:

identifying points in the visual field that are damaged;
removing the damaged points from the visual field;
analyzing the remaining points within the visual field to generate the eye difference estimate and fit the individualized HoV model.

17. The VFA method of claim 16 wherein one of a least-squares algorithm, maximum-likelihood algorithm, Bayesian algorithm, or Machine Learning algorithm are used to generate the eye difference estimate and fit the individualized HoV model.

18. The VFA method of claim 12 wherein the average HoV model includes a combination of an intercept/age model, an eccentricity model, and a visual field asymmetry model.

19. A tangible, non-transitory computer-readable medium storing instructions for automatically assessing visual field testing, that when executed by one or more processors cause the one or more processors to:

generate an eye difference estimate for a test subject relative to reference data for an average healthy eye obtained from a normative dataset, the eye difference estimate indicating a difference in (1) overall sensitivity or general height (GH) and (2) the rate of sensitivity decay with eccentricity (distance from the fovea) relative to the reference data;
generate an individualized HoV model based on the eye difference estimate and an average HoV model saved in a computer memory;
display, on a headset device, a respective stimulus to the test subject at a plurality of test locations, wherein the headset device comprises a display screen positioned proximate to, or within a viewable distance from a user's eyes;

US 12,697,022 B2

45 store in computer memory responses of the test subject to the respective stimulus displayed at the plurality of test locations;

analyze the responses to determine a respective sensitivity value for the test subject at each of the plurality of test locations;

determine total-deviation values for the test subject by subtracting the respective sensitivity value for each of the plurality of test locations from a corresponding value of the individualized HoV model;

analyze the total-deviation values; and provide feedback to the test subject based on the analysis.

20. The tangible, non-transitory computer-readable medium of claim 19 wherein the average HoV model includes a combination of an intercept/age model, an eccentricity model, and a visual field asymmetry model.

* * * * *